US011046778B2

(12) United States Patent
Kato et al.

(10) Patent No.: US 11,046,778 B2
(45) Date of Patent: Jun. 29, 2021

(54) ANTI-PODOCALYXIN ANTIBODY THAT TARGETS TUMOR MICROENVIRONMENT

(71) Applicants: Tohoku University, Miyagi (JP); ZENOAQ RESOURCE CO., LTD., Fukushima (JP)

(72) Inventors: Yukinari Kato, Miyagi (JP); Mika Kato, Miyagi (JP); Satoshi Ogasawara, Miyagi (JP)

(73) Assignees: TOHOKU UNIVERSITY, Miyagi (JP); ZENOAQ RESOURCE CO., LTD., Fukushima (JP)

( * ) Notice: Subject to any disclaimer, the term of this patent is extended or adjusted under 35 U.S.C. 154(b) by 422 days.

(21) Appl. No.: 16/088,941

(22) PCT Filed: Mar. 31, 2016

(86) PCT No.: PCT/JP2016/060822
§ 371 (c)(1),
(2) Date: Mar. 18, 2019

(87) PCT Pub. No.: WO2017/168726
PCT Pub. Date: Oct. 5, 2017

(65) Prior Publication Data
US 2019/0211108 A1 Jul. 11, 2019

(51) Int. Cl.
| | |
|---|---|
| *A61K 39/00* | (2006.01) |
| *C07K 16/28* | (2006.01) |
| *C12N 5/10* | (2006.01) |
| *C12N 15/09* | (2006.01) |
| *C07K 16/32* | (2006.01) |
| *A61K 39/395* | (2006.01) |
| *A61P 35/00* | (2006.01) |

(52) U.S. Cl.
CPC ........ *C07K 16/2896* (2013.01); *A61K 39/395* (2013.01); *A61P 35/00* (2018.01); *C07K 16/32* (2013.01); *C12N 5/10* (2013.01); *C12N 15/09* (2013.01); *C07K 2317/41* (2013.01)

(58) Field of Classification Search
CPC .... C07K 16/2896; A61K 39/395; A61P 35/00
See application file for complete search history.

(56) References Cited

U.S. PATENT DOCUMENTS

| | | | | |
|---|---|---|---|---|
| 7,919,086 B2 * | 4/2011 | Nakano | ................. | C07K 14/47 424/133.1 |
| 9,175,078 B2 * | 11/2015 | Arvedson | ........... | A61K 39/3955 |
| 2003/0115614 A1 | 6/2003 | Kanda et al. | | |
| 2006/0294607 A1 | 12/2006 | Fitzhugh et al. | | |
| 2015/0037328 A1 * | 2/2015 | Liu | ......................... | A61P 35/00 424/133.1 |
| 2015/0309030 A1 | 10/2015 | Jirstrom | | |
| 2016/0347834 A1 | 12/2016 | Kato | | |
| 2017/0219590 A1 | 8/2017 | Atsushi et al. | | |
| 2018/0134786 A1 | 5/2018 | Kato et al. | | |

FOREIGN PATENT DOCUMENTS

| | | |
|---|---|---|
| JP | 2016508219 A | 3/2016 |
| WO | 2002031140 A1 | 4/2002 |
| WO | 2015035190 A1 | 3/2015 |
| WO | 2015053381 A1 | 4/2015 |
| WO | 2015058301 A1 | 4/2015 |
| WO | 2015059159 A1 | 4/2015 |
| WO | 2016013597 A1 | 1/2016 |
| WO | 2016014595 A1 | 1/2016 |

OTHER PUBLICATIONS

Paul, Fundamental Immunology, 3rd Edition, 1993, pp. 292-295 (Year: 1993).*
Rudikoff et al(Proc. Natl. Acad. Sci. USA 1982 vol. 79: p. 1979). (Year: 1982).*
Pascalis et al (The Journal of Immunology (2002) 169, 3076-3084) (Year: 2002).*
Casset et al. (2003) BBRC 307, 198-205 (Year: 2003).*
Brown et al J. Immunol. May 1996; 156(9):3285-3291 (Year: 1996).*
Vajdos et al (J. Mol. Biol. Jul. 5, 2002;320(2); 415-428) (Year: 2002).*
Kataja et al., Ann Oncol 2009; 20(sup 4): iv10-14 (Year: 2009).*
Nelson et al., Ann. Intern Med. 2009; 151:727-737 (Year: 2009).*
Balmana et al. Ann Oncol 2009; 20(supp 4):iv19-20 (Year: 2009).*
Hayatsu, et al., "Podocalyxin expression in malignant astrocytic tumors", Sep. 19, 2008, pp. 394-398, vol. 374, No. 2, Publisher: Biochem Biophys Res Commun.
Kato et al., "A cancer-specific monoclonal antibody against podocalyxin developed by CasMab technology inhibited the tumor growth by antibody dependent cellular . . . ", Jul. 2016, p. 2958, vol. 76, No. 14, Supplement, Publisher: Cancer research; 107th Annual Meeting of the American-Association-of-Cancer-Research (AACR).
Rodriguez et al., "Production and characterization of murine monoclonal antibodies against human podocalyxin", Nov. 7, 2006, pp. 407-417, vol. 68, No. 5, Publisher: Tissue Antigens.
Shunsuke et al, "Anti-podocalyxin antibody exerts antitumor effects via antibody-dependent cellular cytotoxicity in mouse xenograft models of oral squamous cell car . . . ", Apr. 27, 2018, pp. 22480-22497, vol. 9, No. 32, Publisher: Oncotarget.
Yamada et al., "Anti-Podocalyxin Monoclonal Antibody 47-mG2a Detects Lung Cancers by Immunohistochemistry", Apr. 1, 2018, p. 91-94, vol. 37, No. 2, Publisher: Monoclonal Antibodies in Immunodiagnosis and Immunotherapy.
International Search Report received in PCT/JP2016/060822 dated Jun. 28, 2016.
Written Opinion received in PCT/JP2016/060822 dated Jun. 28, 2016.

(Continued)

*Primary Examiner* — Sheela J. Huff
(74) *Attorney, Agent, or Firm* — Suzannah K. Sundby, Esq.; Canady + Lortz LLP

(57) ABSTRACT

The present invention provides a cancer microenvironment-targeting anti-podocalyxin antibody or antigen binding fragment thereof.

19 Claims, 3 Drawing Sheets
Specification includes a Sequence Listing.

(56) References Cited

OTHER PUBLICATIONS

Barderas et al., "In-depth Characterization of the Secretome of Colorectal Cancer Metastatic Cells Identifies Key Proteins in Cell Adhesion, Migration, and Invasion", Jun. 1, 2013, p. 1602-1620, vol. 12, No. 6, Publisher: Molecular & Cellular Proteomics.

Buganim et al., "Transcriptional activity of ATF3 in the stromal compartment of tumors promotes cancer progression", Dec. 1, 2011, p. 1749-1757, vol. 32, No. 12, Publisher: Carcinogenesis.

Casey, et al., "Podocalyxin variants and risk of prostate cancer and tumor aggressiveness", Mar. 1, 2006, pp. 735-741, vol. 15, No. 5, Publisher: Hum Mol Genet.

Cipollone, et al., "The anti-adhesive mucin podocalyxin may help initiate the transperitoneal metastasis of high grade serous ovarian carcinoma", Mar. 1, 2012, pp. 239-252, vol. 29, No. 3, Publisher: Clin Exp Metastasis.

Dallas, et al., "Sialofucosylated podocalyxin is a functional E- and L-selectin ligand expressed by metastatic pancreatic cancer cells", Sep. 15, 2012, pp. C616-C624, vol. 303, No. 6, Publisher: Am J Physiol Cell Physiol.

Kerjaschki et al., "Identification and characterization of podocalyxin—the major sialoprotein of the renal glomerular epithelial cell", Apr. 1, 1984, pp. 1591-1596, vol. 98, No. 4, Publisher: J Cell Biol.

Kerjaschki, et al., "Identification of a major sialoprotein in the glycocalyx of human visceral glomerular epithelial cells", Nov. 1, 1986, pp. 1142-1149, vol. 78, No. 5, Publisher: J Clin Invest.

Larsson, et al., "Overexpression of podocalyxin-like protein is an independent factor of poor prognosis in colorectal cancer", Aug. 23, 2011, pp. 666-672, vol. 105, No. 5, Publisher: Br J Cancer.

Ogasawara, et al., "Podoplanin ni Taisuru Gan Tokuiteki Kotai (CasMab) no Kaihatsu", "Development of Cancer-Specific Antibody (CasMab) against Podoplanin, 87th Annual Meeting", Oct. 18, 2014, p. 4T13a-14 (4P-031), vol. 87, Publisher: The Japanese Biochemical Society.

Schopperle, et al., "Human embryonal carcinoma tumor antigen, Gp200/GCTM-2, is podocalyxin", Jan. 10, 2003, pp. 285-290, vol. 300, No. 2, Publisher: Biochemical and Biophysical Research Communications.

Schopperle, et al., "The TRA-1-60 and TRA-1-81 human pluripotent stem cell markers are expressed on podocalyxin in embryonal carcinoma", Mar. 1, 2007, pp. 723-730, vol. 25, No. 3, Publisher: Stem Cells.

Snyder, et al., "Podocalyxin enhances breast tumor growth and metastasis and is a target for monoclonal antibody therapy", Mar. 27, 2015, p. 46 vol. 17, No. 1, Publisher: Breast Cancer Res.

Somasiri, et al., "Overexpression of the anti-adhesin podocalyxin is an independent predictor of breast cancer progression", Aug. 1, 2004, pp. 5068-5073, vol. 64, No. 15, Publisher: Cancer Research.

Takeda, et al, "Loss of glomerular foot processes is associated with uncoupling of podocalyxin from the actin cytoskeleton", Jul. 1, 2001, pp. 289-301, vol. 108, No. 2, Publisher: J Clin Invest.

Tateno, et al., "Podocalyxin is a glycoprotein ligand of the human pluripotent stem cell-specific probe rBC2LCN", Apr. 1, 2013, pp. 265-273, vol. 2, No. 4, Publisher: Stem Cells Transl Med.

Testa, et al., "Ubiquitous yet distinct expression of podocalyxin on vascular surfaces in normal and tumor tissues in the rat.", Jan. 10, 2009, pp. 311-324, vol. 46, No. 4, Publisher: J Vasc Res.

Thomas, et al., "Podocalyxin-like protein is an E-/L-selectin ligand on colon carcinoma cells: comparative biochemical properties of selectin ligands in host and tumor", Mar. 1, 2009, pp. C505-13, vol. 296, No. 3, Publisher: Am J Physiol Cell Physiol.

Yasuda, et al., "Rab27 effector Slp2-a transports the apical signaling molecule podocalyxin to the apical surface of MDCK II cells and regulates claudin-2 expression", Aug. 15, 2012, pp. 3229-3239, vol. 23, No. 16, Publisher: Mol Biol Cell.

* cited by examiner

1A

1B

2A

2B

3A

3B

ANTI-PODOCALYXIN ANTIBODY THAT TARGETS TUMOR MICROENVIRONMENT

TECHNICAL FIELD

The present invention relates to a cancer microenvironment-targeting anti-podocalyxin antibody.

BACKGROUND ART

Podocalyxin is a type I transmembrane protein discovered in renal glomerular epithelial cells (podocytes) (Non-Patent Document 1). Podocalyxin is composed of 558 amino acid residues and has high homology with CD34 which is a hematopoietic stem cell marker. Podocalyxin has, in an extracellular region thereof, an N-linked glycosylation site, a glycosaminoglycan attachment site, and an O-linked glycosylation site (mucin domain) having a sialic acid rich terminal and is therefore a heavily glycosylated sialomucin. Because of glycosylation differing depending on the tissue in which podocalyxin is expressed, podocalyxin is a glycoprotein having a molecular weight different within a range of from 150 to 200 kDa. Podocalyxin is involved in cell adhesion, morphogenesis, cancer progression, and the like.

Podocalyxin is negatively charged by glycosylation with a sialic acid, a sulfate group, or the like and inhibits cell adhesion. On the other hand, podocalyxin binds to a cytoskeleton protein or the like and is involved closely in the filtering function of kidneys. It also functions as an adhesion molecule (Non-Patent Document 2).

It has been revealed in recent years that in MDCKII cells, a low-molecular-weight G protein Rab and an effector molecule thereof are involved in polarized trafficking of podocalyxin and due to the negative charges generated thereby, podocalyxin takes part in lumen formation (Non-Patent Document 3).

It has been reported that podocalyxin is highly expressed in testicular tumor (Non-Patent Document 4), breast cancer (Non-Patent Document 5), prostate cancer (Non-Patent Document 6), ovarian cancer (Non-Patent Document 7), colorectal cancer (Non-Patent Document 8), and pancreatic cancer (Non-Patent Document 9) and it is a marker of malignancy or poor prognosis. Sugar chains on podocalyxin expressed in cancer cells become a ligand for an E-, P-, or L-selectin expressed on epithelial cells and are involved in adhesion, infiltration, or metastasis of cancer cells (Non-Patent Documents 9 and 10).

In addition, podocalyxin is expressed in undifferentiated cells. It has recently been reported that TRA-1-60 or TRA-1-81 which is a marker of undifferentiated cells is an antibody using, as an epitope, keratan sulfate on podocalyxin but reactivity with podocalyxin disappears by induced differentiation of cells (Non-Patent Document 11). BC2L-C which is a lectin purified from *Burkholderia cenocepacia* is a marker of undifferentiated cells and it specifically binds to a type O sugar chain on podocalyxin (Non-Patent Document 12). These findings suggest that glycosylation on podocalyxin reflects differentiation of undifferentiated cells, malignancy in cancer cells, or the like.

Podocalyxin is known to be expressed in intravascular cells (Non-patent Document 1). The anti-podocalyxin antibodies already developed show good reactivity with these intravascular cells (Non-patent Document 13).

In the interstitium of cancer, fibroblasts, blood vessels, lymphatic vessels, inflammatory cells, immune cells, and connective tissues construct a characteristic microenvironment. As cancers have their own individuality, the microenvironment surrounding them is also extremely diverse. Growth, infiltration, and metastasis of cancer are thought to be deeply related to not only the characteristics of cancer cells but also the mutual relationship between cancer cells and the microenvironment thereof. It has been suggested in recent years that blood vessels in the cancer microenvironment are different from normal blood vessels. In fact, bevacizumab which is an antibody medicament against VEGF restores the abnormal blood vessels in the cancer microenvironment to normal blood vessels as its important mechanism of action and therapy targeting the abnormal blood vessels in the cancer microenvironment has attracted attentions.

CITATION LIST

Non-Patent Document

Non-Patent Document 1: Kerjaschki D et al., J Clin Invest. 1986; 78(5): 1142-1149.
Non-Patent Document 2: Takeda T et al., J Clin Invest. 2001; 108(2): 289-301.
Non-Patent Document 3: Yasuda K et al., Mol Biol Cell. 2012; 23(16): 3229-3239.
Non-Patent Document 4: Schopperle W M et al., Biochem Biophys Res Commun. 2003; 300(2): 285-290.
Non-Patent Document 5: Somasiri A et al., Cancer Res. 2004; 64(15): 5068-5073.
Non-Patent Document 6: Casey G et al., Hum Mol Genet. 2006; 15(5): 735-741.
Non-Patent Document 7: Cipollone J A et al., Clin Exp Metastasis. 2012; 29(3): 239-252.
Non-Patent Document 8: Larsson A et al., Br J Cancer. 2011; 105(5): 666-672.
Non-Patent Document 9: Dallas M R et al., Am J Physiol Cell Physiol. 2012; 303(6): C616-C624.
Non-Patent Document 10: Thomas S N et al., Am J Physiol Cell Physiol. 2009; 296(3): C505-0513.
Non-Patent Document 11: Schopperle W M et al., Stem Cells. 2007; 25(3): 723-730.
Non-Patent Document 12: Tateno H et al., Stem Cells Transl Med. 2013; 2(4): 265-273.
Non-Patent Document 13: Kerjaschki D et al., J Cell Biol. 1984 April; 98(4):1591-1596.

SUMMARY

Technical Problem

An antibody specifically binding only to podocalyxin expressed in a cancer microenvironment, if any, is presumed to be useful as a medicament, a diagnostic agent, a reagent, or the like.

The technical problem of the present invention is to provide a novel cancer microenvironment-targeting anti-podocalyxin antibody.

Solution to Problem

The present inventors have developed a CasMab method as a method of preparing a cancer-specific antibody. By this CasMab method, not only a cancer-specific antibody can be prepared but also an antibody that recognizes the three-dimensional structure of a membrane protein or an antiglycopeptide antibody containing, in the epitope thereof, both a sugar chain and a peptide can be prepared.

The present inventors have considered that a novel cancer microenvironment-targeting anti-podocalyxin antibody can be established by preparing, using the CasMab method, an anti-podocalyxin antibody that reacts with only abnormal blood vessels but does not react with normal blood vessels.

As a result of carrying out an extensive investigation with a view to overcoming the above problem, the present inventors have succeeded in the establishment of a novel cancer microenvironment-targeting anti-podocalyxin antibody by preparing an anti-podocalyxin antibody that reacts only with abnormal blood vessels but does not react with normal blood vessels.

The present invention is as shown below.

[1] A cancer microenvironment-targeting anti-podocalyxin antibody of any of the following (i) to (iii) or an antigen-binding fragment thereof,
(i) having at least one of the following six CDRs:

```
a heavy chain CDR1:
                              (SEQ ID NO: 2)
GYSFTDY, a heavy chain CDR2:
                              (SEQ ID NO: 3)
NPRNGG, a heavy chain CDR3:
                              (SEQ ID NO: 4)
EAMEY, a light chain CDR1:
                              (SEQ ID NO: 5)
KSSQSLLDSAGKTYLN, a light chain CDR2:
                              (SEQ ID NO: 6)
RLMYLVSKLA,
and a light chain CDR3:
                              (SEQ ID NO: 7)
WQGTHFPRT;
```

(ii) having, as the heavy chains CDR 1 to 3 and the light chains CDR 1 to 3 shown in (i), at least one of the heavy chains CDR 1 to 3 and the light chains CDR 1 to 3 including addition, substitution, or deletion of from one to several amino acids; and
(iii) having, as at least one of the heavy chains CDR 1 to 3 and the light chains CDR 1 to 3, an amino acid sequence exhibiting 80% or more identity with the amino acid sequence of the heavy chains CDR1 to 3 and the light chains CDR1 to 3 shown in (i).

[2] A cancer microenvironment-targeting anti-podocalyxin antibody having:
a heavy chain having an amino acid sequence represented by SEQ ID NO: 10;
a heavy chain having, as the amino acid sequence represented by SEQ ID NO: 10, an amino acid sequence including addition, substitution, or deletion of from one to several amino acids; or
a heavy chain having an amino acid sequence exhibiting 80% or more identity with the amino acid sequence represented by SEQ ID NO: 10; or an antigen-binding fragment of the antibody.

[3] A cancer microenvironment-targeting anti-podocalyxin antibody having:
a light chain having an amino acid sequence represented by SEQ ID NO: 8,
a light chain having, as the amino acid sequence represented by SEQ ID NO: 8, an amino acid sequence including addition, substitution, or deletion of from one to several amino acids; or
a light chain having an amino acid sequence exhibiting 80% or more identity with the amino acid sequence represented by SEQ ID NO: 8; or an antigen-binding fragment of the antibody.

[4] The cancer microenvironment-targeting anti-podocalyxin antibody or the antigen-binding fragment thereof described in any of from [1] to [3], wherein one or more N-linked sugar chains are bound to an Fc region and no fucose is bound to N-acetylglucosamine at a reducing end of the N-linked sugar chains.

[5] A nucleic acid encoding any one of the heavy chains CDR1 to 3 and the light chains CDR 1 to 3 described above in [1].

[6] A nucleic acid encoding any one of the heavy chains described in [2] and the light chains described in [3].

[7] An expression vector having the nucleic acid described in [5] or [6].

[8] A transformant having the expression vector described in [7].

[9] A pharmaceutical composition having, as an active ingredient thereof, the cancer microenvironment-targeting anti-podocalyxin antibody or the antigen-binding fragment thereof described in any of from [1] to [4].

[10] A pharmaceutical composition having, as an active ingredient thereof, the cancer microenvironment-targeting anti-podocalyxin antibody or the antigen-binding fragment thereof described in any of from [1] to [4] to which a substance having an anti-cancer activity has been bound.

[11] The pharmaceutical composition described in [9] or [10], which is a preventive or therapeutic agent for cancer.

Advantageous Effects of Invention

By a method for producing the antibody according to the present invention, a novel cancer microenvironment-targeting anti-podocalyxin antibody can be obtained.

BRIEF DESCRIPTION OF DRAWINGS

FIG. 4F shows vascular endothelial cells. FIG. 4A shows that the renal normal blood vessels and glomeruli are stained with PcMab-47 and FIG. 4B shows that neither the renal normal blood vessels nor the renal glomeruli are stained with PcMab-60. FIG. 4C shows that the normal blood vessels in the small intestine are stained with PcMab-47 and FIG. 4D shows that the normal blood vessels in the small intestine are not stained with PcMab-60. FIG. 4E shows that not only the cancer cells in the breast cancer tissues but also the blood vessels therearound are stained with PcMab-47 and FIG. 4F shows that the abnormal blood vessels around the cancer cells in the breast cancer tissues are stained with PcMab-60.

DESCRIPTION OF EMBODIMENTS

Figure 1:
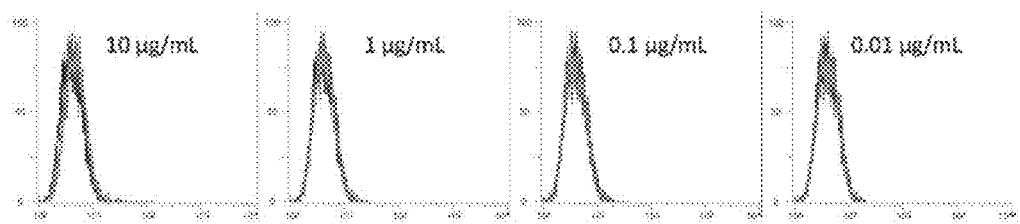
FIG. 1A shows the flow cytometry results, at each concentration, of PcMab-60, that is, a cancer microenvironment-targeting anti-podocalyxin antibody, which is an antibody against podocalyxin, by using a human glioblastoma cell line LN229.
FIG. 1B shows the flow cytometry results, at each concentration, of PcMab-60 by using podocalyxin forcibly-expressed LN229 (LN229/hPODXL).
Figure 1:
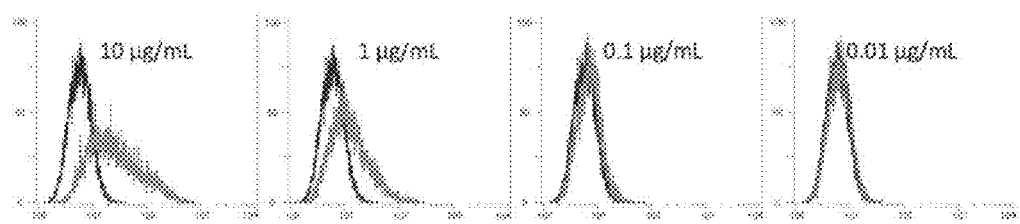

The present invention will be described specifically by the embodiments. The present invention is not limited by the following embodiments but can be modified by various ways.

The cancer microenvironment-targeting anti-podocalyxin antibody or antigen-binding fragment thereof according to the present invention is any of the following (i) to (iii):

(i) having at least one of the following six CDRs:

```
a heavy chain CDR1:
                       (SEQ ID NO: 2)
GYSFTDY, a heavy chain CDR2:
                       (SEQ ID NO: 3)
NPRNGG, a heavy chain CDR3:
                       (SEQ ID NO: 4)
EAMEY, a light chain CDR1:
                       (SEQ ID NO: 5)
KSSQSLLDSAGKTYLN, a light chain CDR2:
                       (SEQ ID NO: 6)
RLMYLVSKLA,
and a light chain CDR3:
                       (SEQ ID NO: 7)
WQGTHFPRT;
```

(ii) having, as the heavy chains CDR 1 to 3 and the light chains CDR 1 to 3 shown in (i), at least one of the heavy chains CDR 1 to 3 and the light chains CDR 1 to 3 including addition, substitution, or deletion of from one to several amino acids; and (iii) having, as at least one of the heavy chains CDR 1 to 3 and the light chains CDR 1 to 3, an amino acid sequence exhibiting 80% or more identity with the amino acid sequence of the heavy chains CDR1 to 3 and the light chains CDR1 to 3 shown in (i).

The cancer microenvironment-targeting anti-podocalyxin antibody or antigen-binding fragment thereof according to the present invention is an anti-podocalyxin antibody which reacts with only abnormal blood vessels and does not react with normal blood vessels.

In the present specification, the "antibody" has a structure having two heavy chains (H chains) and two light chains (L chains) associated with each other while being stabilized via a pair of disulfide bonds. The heavy chain is composed of a heavy-chain variable region VH, heavy-chain constant regions CH1, CH2 and CH3, and a hinge region positioned between CH1 and CH2. The light chain is composed of a light-chain variable region VL and a light-chain constant region CL. Among these, a variable region fragment (Fv) composed of VH and VL is a region which is directly involved in antigen binding and imparts the antibody with diversity. Further, an antigen-binding region composed of VL, CL, VH and CH1 is called a Fab region, and a region composed of a hinge region, CH2 and CH3 is called an Fc region.

Of the variable regions, a region in direct contact with an antigen shows particularly large variation and is called "complementarity-determining region" (CDR). A region other than CDR and showing relatively smaller variation is called "framework region" (FR). The light chain variable region and the heavy chain variable region each have three CDRs (heavy chains CDR1 to 3 and light chains CDR1 to 3).

The cancer microenvironment-targeting anti-podocalyxin antibody of the present invention may be either a monoclonal antibody or a polyclonal antibody. The cancer microenvironment-targeting anti-podocalyxin antibody of the present invention may be any isotype of IgG, IgM, IgA, IgD, and IgE. It may be obtained by immunizing a non-human animal such as mouse, rat, hamster, guinea pig, rabbit, or chicken or it may be a recombinant antibody. It may also be a chimeric antibody, a humanized antibody, a fully humanized antibody, or the like.

The term "chimeric antibody" means an antibody obtained by linking a fragment of an antibody derived from a different species.

The term "humanized antibody" means an antibody obtained by substituting, by an amino acid sequence characteristic to a non-human-derived antibody, a position of a human antibody corresponding thereto. Examples of it include antibodies having the heavy chains CDR1 to 3 and the light chains CDR1 to 3 of an antibody prepared by immunizing a mouse and having, as all the other regions including four respective framework regions (FR) of the heavy chains and light chains, those derived from the human antibody. Such an antibody may also be called "CDR grafted antibody". The term "humanized antibody" may include a human chimeric antibody.

The term "antigen-binding fragment" of the cancer microenvironment-targeting anti-podocalyxin antibody as used herein means a fragment of the cancer microenvironment-targeting anti-podocalyxin antibody that binds to podocalyxin. Specific examples include, but are not limited to, Fab composed of VL, VH, CL, and CH1 regions; F(ab')2 having two Fabs connected via a disulfide bond in a hinge region; Fv composed of VL and VH; a single-chain antibody scFv having VL and VH connected to each other via an artificial polypeptide linker; and bispecific antibodies such as diabody, scDb, tandem scFv, and leucine zipper type ones.

In one aspect, the cancer microenvironment-targeting anti-podocalyxin antibody or antigen-binding fragment thereof according to the present invention has at least one of the following six CDRs. These CDRs are CDR sequences of PcMab-60, a cancer microenvironment-targeting anti-podocalyxin antibody, which is an antibody against podocalyxin, obtained in Example.

```
Heavy chain CDR1:
                    (SEQ ID NO: 2)
GYSFTDY

Heavy chain CDR2:
                    (SEQ ID NO: 3)
NPRNGG

Heavy chain CDR3:
                    (SEQ ID NO: 4)
EAMEY

Light chain CDR1:
                    (SEQ ID NO: 5)
KSSQSLLDSAGKTYLN

Light chain CDR2:
                    (SEQ ID NO: 6)
RLMYLVSKLA

Light chain CDR3:
                    (SEQ ID NO: 7)
WQGTHFPRT
```

The cancer microenvironment-targeting anti-podocalyxin antibody or antigen-binding fragment thereof according to the present invention may have at least one of the above-described six CDRs insofar as it produces the advantage of the present invention. It may have two or more, three or more, four or more, five or more or six CDRs. The greater the number of CDRs, the more preferable.

The cancer microenvironment-targeting anti-podocalyxin antibody or antigen-binding fragment thereof according to the present invention may have at least one of the chain CDR1 including, in the amino acid sequence represented by SEQ ID NO: 2, addition, substitution, or deletion of from one to several amino acids; the heavy chain CDR2 including, in the amino acid sequence represented by SEQ ID NO: 3, addition, substitution, or deletion of from one to several amino acids; the heavy chain CDR3 including, in the amino acid sequence represented by SEQ ID NO: 4, addition, substitution, or deletion of from one to several amino acids; the light chain CDR1 including, in the amino acid sequence represented by SEQ ID NO: 5, addition, substitution, or deletion of from one to several amino acids; the light chain CDR2 including, in the amino acid sequence represented by SEQ ID NO: 6, addition, substitution, or deletion of from one to several amino acids; and the light chain CDR3 including, in the amino acid sequence represented by SEQ ID NO: 7, addition, substitution, or deletion of from one to several amino acids.

When the heavy chains CDR1 to 3 (SEQ ID NOS: 2 to 4) and the light chains CDR1 to 3 (SEQ ID NOS: 5 to 7) have at least one of the heavy chains CDR1 to 3 and the light chains CDR 1 to 3 including addition, substitution, or deletion of from one to several amino acids, the at least one of the heavy chains CDR1 to 3 and the light chains CDR1 to 3 including addition, substitution, or deletion of from one to several amino acids preferably retains a function as CDR, in other words, retains a function of reacting with only abnormal blood vessel and not reacting with normal blood vessels.

In the present specification, the term "amino acid" is used in its broadest meaning and it encompasses not only naturally occurring amino acids but also artificial amino acid variants and derivatives of them. The amino acids may be represented by a commonly used single-letter or three-letter code. In the present specification, examples of the amino acids or derivatives thereof include naturally occurring proteinogenic L-amino acids, non-naturally occurring amino acids, and chemically synthesized compounds having properties known in the art as characteristics of an amino acid. Examples of the non-naturally occurring amino acids include, but are not limited to, α,α-disubstituted amino acids (such as α-methylalanine), N-alkyl-α-amino acids, D-amino acids, β-amino acids, and α-hydroxy acids, each having a main chain structure different from that of naturally occurring amino acids; amino acids (such as norleucine and homohistidine) having a side-chain structure different from that of naturally occurring amino acids; amino acids (such as "homo" amino acids, homophenylalanine, and homohistidine) having extra methylene in the side chain thereof; and amino acids (such as cysteic acid) obtained by substituting a carboxylic acid functional group in the side chain by a sulfonic acid group.

When the term "including addition, substitution, or deletion of from one to several amino acids" is used herein, the number of amino acids to be deleted, substituted, or the like is not particularly limited insofar as the resulting polypeptide retains its function as a CDR. The number of amino acids can be set, for example, at 1, 2, 3, 4, 5, 6, 7, 8, 9, or 10, preferably at 1, 2, 3, or 4. The amino acid to be substituted or added may be, as well as a naturally-occurring proteinogenic amino acid, a non-naturally-occurring amino acid or an amino acid analog. The position of deletion, substitution, or addition of the amino acid may be any site in an original CDR sequence insofar as the function as a CDR is retained.

The cancer microenvironment-targeting anti-podocalyxin antibody or antigen-binding fragment thereof according to the present invention may have at least one of a heavy chain CDR1 having an amino acid sequence having 80% or more identity with the amino acid sequence represented by SEQ ID NO: 2; a heavy chain CDR2 having an amino acid sequence having 80% or more identity with the amino acid sequence represented by SEQ ID NO: 3; a heavy chain CDR3 having an amino acid sequence having 80% or more identity with the amino acid sequence represented by SEQ ID NO: 4; a light chain CDR1 having an amino acid sequence having 80% or more identity with the amino acid sequence represented by SEQ ID NO: 5; a light chain CDR2 having an amino acid sequence having 80% or more identity with the amino acid sequence represented by SEQ ID NO: 6; and a light chain CDR3 having an amino acid sequence having 80% or more identity with the amino acid sequence represented by SEQ ID NO: 7.

When the heavy chains CDR1 to 3 (SEQ ID NOS: 2 to 4) and the light chains CDR 1 to 3 (SEQ ID NOS: 5 to 7) have at least one of the heavy chains CDR1 to 3 and the light chains CDR 1 to 3 having an amino acid sequence having 80% or more identity with the amino acid sequence represented by SEQ ID NOS: 2 to 7, the at least one of the heavy chains CDR1 to 3 and the light chains CDR 1 to 3 having an amino acid sequence having 80% or more identity preferably retains a function as a CDR, in other words, retains a function of reacting only with abnormal blood vessels and not reacting with normal blood vessels.

The term "having 80% or more identity" as used herein means that when two polypeptides having an original sequence and a mutated sequence, respectively, are aligned so that their amino acid sequences show the maximum identity, the number of amino acid residues which they have in common is 80% or more of the number of amino acids of the original sequence.

The identity is not limited insofar as it is 80% or more and the function as a CDR can be retained. It can be set, for example, at 85% or more, 90% or more, 91% or more, 92% or more, 93% or more, 94% or more, 95% or more, 96% or more, 97% or more, 98% or more, or 99% or more.

CDRs having an amino acid sequence obtained by adding, substituting, or deleting an amino acid to, by, or from the amino acid sequences of the heavy chains CDR1 to 3 and the light chains CDR1 to 3, or CDRs having an amino acid sequence having 80% or more identity with the amino acid sequences of the heavy chains CDR1 to 3 and the light chains CDR1 to 3 can be prepared using a known method such as site-specific mutagenesis, random mutagenesis, chain shuffling, or CDR walking. It is well known to those skilled in the art that when the above method is used, CDRs with more mature affinity can be obtained by presenting an antibody or antibody fragment having, in the CDR thereof, a variety of mutations on a phage surface by phage display, followed by screening using an antigen (e.g., Wu et al., PNAS. 1998; 95: 6037-6042.; Schier R et al., J. Mol. Bio. 1996; 263: 551-567.; Schier R et al., J. Mol. Biol. 1996; 255: 28-43.; Yang W P et al., J. Mol. Biol. 1995; 254: 392-403).

The cancer microenvironment-targeting anti-podocalyxin antibody or antigen binding fragment thereof according to the present invention has:
a light chain having an amino acid sequence represented by SEQ ID NO: 8,
a light chain having, in the amino acid sequence represented by SEQ ID NO: 8, an amino acid sequence including addition, substitution, or deletion of from one to several amino acids; or
a light chain having an amino acid sequence having 80% or more identity with the amino acid sequence represented by SEQ ID NO: 8.

The amino acid sequence represented by SEQ ID NO: 8 is an amino acid sequence of the light chain of PcMab-60.

The cancer microenvironment-targeting anti-podocalyxin antibody or antigen binding fragment thereof according to the present invention has:
a heavy chain having an amino acid sequence represented by SEQ ID NO: 10,
a heavy chain having, in the amino acid sequence represented by SEQ ID NO: 10, an amino acid sequence including addition, substitution, or deletion of from one to several amino acids; or
a heavy chain having an amino acid sequence having 80% or more identity with the amino acid sequence represented by SEQ ID NO: 10.

The amino acid sequence represented by SEQ ID NO: 10 is an amino acid sequence of the heavy chain of chPcMab-60.

When in the present specification, the amino acid sequence of the heavy chain or light chain includes addition, substitution, or deletion of from one to several amino acids, the number of amino acids to be added, substituted, or deleted can be set at, for example, 1, 2, 3, 4, 5, 6, 7, 8, 9, or 10. Other terms have the same meaning as described above.

The cancer microenvironment-targeting anti-podocalyxin antibody according to the present invention may be an antibody having one or more N-linked sugar chains bound to the Fc region thereof and having no fucose bound to N-acetylglucosamine at the reducing end of the N-linked sugar chain.

For example, the Fc region of an IgG antibody has therein two binding sites of an N-linked sugar chain, to which sites a complex-type sugar chain has been bound. The term "N-linked sugar chain" means a sugar chain to be bound to Asn of an Asn-X-Ser/Thr sequence and has a common structure Man3GlcNAc2-Asn. It is classified into a high mannose type, a hybrid type, a complex type, or the like, depending on the kind of the sugar chain bound to two mannoses (Man) at the non-reducing end.

Although fucose may be bound to N-acetylglucosamine (GlcNAc) at the reducing end of the N-linked sugar chain, it is known that an ADCC activity shows a remarkable increase when fucose is not bound thereto compared with when fucose is bound thereto. This is described in, for example, the pamphlet of WO2002/031140.

Since a remarkable improvement in the ADCC activity may lead to a reduction of a dose of an antibody when it is used as a drug, adverse side effects can be alleviated and at the same time, medical expenses can be reduced.

A substance having an anti-cancer activity may be bound to the cancer microenvironment-targeting anti-podocalyxin antibody of the present invention.

The cancer microenvironment-targeting anti-podocalyxin antibody of the present invention reacts with only abnormal blood vessels and does not react with normal blood vessels so that the anti-podocalyxin antibody can be delivered only to the abnormal blood vessels in the cancer microenvironment. This antibody to which a substance having an anti-cancer activity is bound is useful because it can deliver the compound having an anti-cancer activity only to the abnormal blood vessels in the cancer microenvironment.

The term "substance having an anti-cancer activity" as used herein means a substance which causes at least one of reduction (retardation or stopping) of a tumor size, inhibition of tumor metastasis, inhibition (retardation or stopping) of tumor growth, and alleviation of one or plural symptoms associated with cancer. Specific examples include, but are not limited to, toxins, anti-cancer agents, and radioisotopes.

Examples of toxins having an anti-cancer activity include *Pseudomonas* exotoxin (PE) or a cytotoxic fragment thereof (for example, PE38), a diphtheria toxin, and ricin A. The toxin having an anti-cancer activity exhibits toxicity only to cells into which the toxin is incorporated together with the anti-podocalyxin antibody, that is, cancer cells in which podocalyxin is expressed so that it has an advantage of specifically producing an advantage without adversely affecting cells around them.

Examples of the anti-cancer agent include low molecular weight compounds such as adriamycin, daunomycin, mitomycin, cisplatin, vincristine, epirubicin, methotrexate, 5-fluorouracil, aclacinomycin, nitrogen mustards, cyclophosphamide, bleomycin, daunorubicin, doxorubicin, vincristine, vinblastine, vindesine, tamoxifen, and dexamethasone, and proteins such as cytokines that activate immunocompetent cells. Examples of the cytokines that activate immunocompetent cells include human interleukin 2, human granulocyte-macrophage colony-stimulating factor, human macrophage colony-stimulating factor, and human interleukin 12.

Examples of the radioisotope having an anti-cancer activity include $^{32}P$, $^{14}C$, $^{125}I$, $^{3}H$, $^{131}I$, $^{211}At$, and $^{90}Y$. The radioisotope also exhibits toxicity to cells around cells to which the anti-podocalyxin antibody binds, that is, podocalyxin expression cells. In general, cancer cells are not uniform and podocalyxin is not expressed in every cancer cell so that radioisotopes are useful for killing podocalyxin-negative cancer cells around them. Further, when a radioisotope is bound, it may be bound to the fragment of the anti-podocalyxin antibody such as Fab or scFv.

The substance having an anti-cancer activity may be directly bound to the cancer microenvironment-targeting anti-podocalyxin antibody by a known method. It may be, for example, bound to the cancer microenvironment-targeting anti-podocalyxin antibody after being enclosed in a carrier such as liposome.

When the substance having an anti-cancer activity is a protein or a polypeptide, by linking a nucleic acid (which will be described later) encoding the cancer microenvironment-targeting anti-podocalyxin antibody of the present invention with a DNA encoding the substance having an anti-cancer activity and inserting the resulting linked product into an appropriate expression vector, the substance having an anti-cancer activity and the cancer microenvironment-targeting anti-podocalyxin antibody may be expressed as a fusion protein.

(Nucleic Acid)

The present invention embraces a nucleic acid encoding the cancer microenvironment-targeting anti-podocalyxin antibody of the present invention. The nucleic acid may be either a naturally occurring nucleic acid or an artificial nucleic acid. Examples include, but are not limited to, DNA, RNA, and a DNA/RNA chimera. The base sequence of the nucleic acid encoding the cancer microenvironment-targeting anti-podocalyxin antibody can be determined by a method known to those skilled in the art or a method based thereon and can be prepared by a known method or a method based thereon.

Examples of the nucleic acid encoding the cancer microenvironment-targeting anti-podocalyxin antibody of the present invention include, but are not limited to, a DNA (SEQ ID NO: 11) encoding the heavy chain of chPcMab-60 represented by SEQ ID NO: 10 and a DNA (SEQ ID NO: 9) encoding the light chain of PcMab-60 represented by SEQ ID NO: 8.

The nucleic acids encoding respective CDRs of PcMab-60 are included in the DNA sequences represented by these SEQ ID NOS.

(Expression Vector)

The present invention also embraces an expression vector containing the nucleic acid encoding the cancer microenvironment-targeting anti-podocalyxin antibody of the present invention. The expression vector can be selected as needed according to a host cell to be used. Examples include a plasmid, a retrovirus vector, an adenovirus vector, an adeno-associated virus (AAV) vector, a plant virus vector such as cauliflower mosaic virus vector or tobacco mosaic virus vector, a cosmid, a YAC, and an EBV-derived episome. The nucleic acid encoding the cancer microenvironment-targeting anti-podocalyxin antibody of the present invention can be inserted into these expression vectors by a known method (such as a method using a restriction enzyme).

The expression vector of the present invention may further contain a promoter for controlling the expression of an antibody gene, a replication origin, a selection marker gene, or the like. The promoter and the replication origin may be selected as needed, depending on the nature of the host cell and expression vector.

(Transformant)

The present invention embraces a transformant containing the expression vector of the present invention. The transformant can be obtained by transfecting the expression vector of the present invention into appropriate host cells. Examples of the usable host cells include eukaryotic cells such as mammalian cells (CHO cells, COS cells, myeloma cells, HeLa cells, Vero cells, and the like), insect cells, plant cells, and fungus cells (*Saccharomyces, Aspergillus,* and the like), and prokaryotic cells such as *Escherichia coli* (*E. coli*) and *Bacillus subtilis*.

The cancer microenvironment-targeting anti-podocalyxin antibody according to the present invention can be produced, for example, by carrying out screening by immunohistochemistry at the time when an antibody against podocalyxin expressed specifically in cancer cells (a cancer cell-specific anti-podocalyxin antibody) is obtained by the CasMab method.

The method for producing a cancer cell-specific anti-podocalyxin antibody includes:
a step of introducing a nucleic acid encoding all or a portion of podocalyxin into cells expressing a cancer cell-specific sugar chain structure and thereby causing expression of cancer cell-specific podocalyxin or a portion thereof;
a step of immunizing a non-human mammal with the cancer cell-specific podocalyxin or portion thereof to obtain antibodies; and
a step of purifying the antibodies by primary screening using a purified cancer cell-specific podocalyxin or a portion thereof.

The term "cancer cell-specific anti-podocalyxin antibody" as used herein means an antibody having significantly higher reactivity with podocalyxin expressed in cancer cells than reactivity with podocalyxin expressed in normal cells. In one aspect, the "cancer cell-specific anti-podocalyxin antibody" reacts with podocalyxin expressed in cancer cells but never reacts with podocalyxin expressed in normal cells. In another aspect, the "cancer cell-specific anti-podocalyxin antibody" has markedly high reactivity with podocalyxin expressed in cancer cells, while it reacts to some extent with podocalyxin expressed in normal cells.

Podocalyxin is highly expressed in testicular tumor, breast cancer, prostate cancer, ovarian cancer, colorectal cancer, pancreatic cancer, and the like and it is also expressed in normal cells.

Human podocalyxin (BC143318, NM_001018111) is a protein represented by SEQ ID NO: 1 but the term "podocalyxin" as used herein encompasses, in addition to it, functional mutants thereof.

In the present specification, the "cells expressing a cancer cell-specific sugar chain structure" may be any cells insofar as they express a cancer cell-specific sugar chain structure. For example, they may be cancer cells or cells obtained by introducing a necessary glycosyltransferase into non-cancer cells and thereby artificially modifying them to express a cancer cell-specific sugar chain structure. Examples of the "cells expressing a cancer cell-specific sugar chain structure" include the following cells:

Cells derived from a glioblastoma cell line LN229.

The present inventors have so far confirmed acceleration of keratan sulfate modification depending on the malignancy of cerebral tumor (Kato Y et al., Biochem Biophys Res Commun. 2008; 369(4): 1041-1046) and discovered, from a cerebral tumor cell line, LN229 cells in which high keratan sulfate modification has occurred (Hayatsu N et al., Biochem Biophys Res Commun. 2008; 368(2): 217-222). They have reported that podocalyxin is highly expressed in astrocytic tumor in correlation with the malignancy (Hayatsu N et al., Biochem Biophys Res Commun. 2008; 374(2): 394-398). Further, they have reported cancer cell-specific addition of sialic acid to a protein expressed by LN229 cells (Kato Y et al., Sci Rep. 2014; 4: 5924).

Cells obtained by gene introduction of a glycosyltransferase KSGal6ST into glioblastoma cell line LN464 cells (Hayatsu N et al., Biochem Biophys Res Commun. 2008; 368: 217-222). The present inventors have reported in this document that a highly expressed line of keratan sulfate known to be expressed highly in cerebral tumor tissues can be obtained by gene introduction of a glycosyltransferase KSGal6ST into glioblastoma cell line LN464 cells.

Cells obtained by gene introduction of a glycosyltransferase into cervical cancer cells (HeLa cells) or leukemia cells (Namalwa cells) (Kimura H et al., Biochem Biophys Res Commun. 1997 Aug. 8; 237 (1): 131-137). In this document, the present inventors have observed in detail what sugar chain is added by carrying out gene introduction of a glycosyltransferase into cervical cancer cells (HeLa cells) or leukemia cells (Namalwa cells).

Cells obtained by gene introduction of glycosyltransferase into Namalwa cells (Kaneko M et al., FEBS Lett. 1999; 452(3): 237-242). In this document, the present inventors have observed in detail what sugar chain is added by carrying out gene introduction of a glycosyltransferase into Namalwa cells.

Cells obtained by introduction of glycosyltransferase into simian kidney cells (COS1 cells) (Kaneko M et al., Blood. 1997; 90(2): 839-849).

Cells obtained by introduction of glycosyltransferase into hamster ovarian cells (CHO-Lec1 cells) (Kaneko M et al., FEBS Lett. 2003; 554(3): 515-519).

As the cells expressing a cancer cell-specific sugar chain structure, a Trichostatin A-treated chicken B cell-derived DT40 cell line may be used and as the method for producing an antibody, an Adlib method for obtaining an antibody producing line from the Trichostatin A-treated chicken B cell-derived DT40 cell line (Seo H et al., Nat. Biotechnol. 2002; 6: 731-736) may be used. Alternatively, as the non-human mammal, KM mice which are mice obtained by destroying a mouse antibody gene and introducing a human antibody gene may be used and as the method for producing an antibody, a method of immunizing KM mice to prepare a human antibody (Itoh K et al., Jpn. J. Cancer Res. 2001; 92: 1313-1321; Koide A et al., J. Mol. Biol. 1998; 284: 1141-1151) or the like may be used.

In the present specification, the "step of introducing a nucleic acid encoding all or a portion of podocalyxin into cells expressing a cancer cell-specific sugar chain structure and thereby causing expression" can be performed by those skilled in art in a manner known per se in the art. The method for producing a cancer cell-specific anti-podocalyxin antibody is characterized by that a cancer cell-specific podocalyxin obtained by introducing a nucleic acid encoding all or a portion of podocalyxin into cancer cells to cause forced expression or a portion thereof is used as an antigen. As the nucleic acid encoding the portion of podocalyxin, a nucleic acid encoding a portion of podocalyxin to which a cancer cell-specific sugar chain has been bound can be used. As the nucleic acid encoding a portion of podocalyxin to which a cancer cell-specific sugar chain has been bound, a nucleic acid encoding the extracellular region of podocalyxin can be used. In the present specification, the nucleic acid may be any nucleic acid insofar as it can express an intended protein. Examples include DNA, RNA, DNA/RNA chimera, and artificial nucleic acids.

In one aspect, all or a portion of podocalyxin is expressed as a secretory type. This can be achieved by introducing a nucleic acid encoding the extracellular region of podocalyxin into cells expressing a cancer cell-specific sugar chain structure. Podocalyxin expressed as a secretory type can be obtained by purifying a culture supernatant of cells expressing a cancer cell-specific sugar chain structure. Purification may be performed, for example, by expressing podocalyxin with a proper tag and purifying it while making use of the tag.

In the present specification, the "step of immunizing a non-human mammal with the cancer cell-specific podocalyxin or portion thereof to obtain antibodies" can be carried out by administering the cancer cell-specific podocalyxin or portion thereof to a non-human mammal. The purified cancer cell-specific podocalyxin or portion thereof may be used.

Immunization can be performed, for example, by subcutaneously, intradermally, intramuscularly, intravenously, or intraperitoneally injecting the cancer cell-specific podocalyxin or portion thereof together with an adjuvant if necessary.

Alternatively, the step of immunizing a non-human mammal may be performed by causing the cancer cell-specific podocalyxin to be expressed not as a secretory type but as a membrane protein and then administering it as the entire cell to the non-human mammal.

The mammal can be immunized in a manner known per se in the art. For example, it can be immunized by intraperitoneally administering from $1 \times 10^7$ to $1 \times 10^9$ cells once/10 days at a plurality of times.

In the present specification, the non-human mammal is typically a mouse but not particularly limited thereto. Examples include rats, hamsters, rabbits, cats, dogs, monkeys, goats, sheep, cows, and horses.

The term "primary screening of the antibodies" as used herein means first screening performed during a procedure of identifying an intended antibody from antibody producing cells. It means, for example, screening using a culture supernatant of a hybridoma producing a monoclonal antibody.

The primary screening of the antibodies preferably includes a step of obtaining a monoclonal antibody and a step of identifying a hybridoma producing the monoclonal antibody.

The primary screening of the antibodies in the present invention is generally performed as follows.

First, podocalyxin or a portion thereof is, together with an affinity tag (FLAG tag, His tag, Myc tag, PA tag, or the like), expressed in cells expressing a cancer cell-specific sugar chain structure and purification is performed using the affinity tag. The cancer cell-specific podocalyxin or portion thereof thus purified is immobilized on an ELISA plate. Then, the antibodies obtained from antibody producing cells are added to the plate and wells in which a reaction has occurred are selected. By this method, cancer cell-specific antibodies can be selected in the initial stage of screening.

The purified cancer cell-specific podocalyxin or portion thereof is not particularly limited insofar as it is a purified protein or a portion thereof. It may be a protein purified after forced expression or a purified endogenic protein.

The method for producing a cancer cell-specific anti-podocalyxin antibody according to the present invention may include, after the primary screening, a step of comparing reactivity of the antibodies with cancer cells or tissues and reactivity with normal cells or tissues and selecting an antibody having the reactivity with cancer cells or tissues dominantly higher than the reactivity with normal cells or tissues.

Examples of the cancer cells or tissues include cells or tissues in cerebral tumor, prostate cancer, testicular tumor, kidney cancer, thyroid gland cancer, bladder cancer, breast cancer, ovarian cancer, colorectal cancer, pancreatic cancer, malignant mesothelioma, and osteosarcoma. Examples of the normal cells include vascular endothelial cells and renal epithelial cells. Examples of the normal tissues include systemic blood vessels and kidney.

Examples of the cancer cells or tissues may also include cells or tissues of 1) adenocarcinoma (lung adenocarcinoma, liver adenocarcinoma, pancreatic adenocarcinoma, lymph adenocarcinoma, uterine adenocarcinoma, seminal vesicle adenocarcinoma, gastric adenocarcinoma, and the like); 2) basal cell carcinoma (skin cancer and the like); 3) squamous cell carcinoma (intraoral cancer, tongue cancer, laryngeal cancer, esophagus cancer, pharyngeal cancer, cervical cancer, and the like); 4) sarcoma (lymphangiosarcoma, Kaposi's sarcoma, malignant osteosarcoma, and the like); 5) hematopoietic organ tumor (leukemia such as acute/chromic myeloid leukemia, acute promyelocytic leukemia, and acute/chronic lymphocytic leukemia, lymphoma such as Hodgkin lymphoma and non-Hodgkin lymphoma, multiple myeloma, and the like); and 6) renal cell cancer and the like.

The "step of comparing reactivity of the antibodies with cancer cells or tissues and reactivity with normal cells or tissues" as used herein means a step of reacting cancer cells or tissues with the antibodies obtained by the primary screening and detecting the presence or absence of a bond therebetween while reacting normal cells or tissues with the antibodies obtained by the primary screening and detecting the presence or absence of a bond therebetween. This step can be performed by flow cytometry, immunohistochemistry (IHC), immunocytochemistry (ICC), or the like.

A cancer cell-specific antibody can be obtained by comparing between the reactivity of the antibody with cancer cells or tissues and the reactivity of the antibody with normal cells or tissues and then selecting an antibody showing significantly higher reactivity with the cancer cells or tissues than with the normal cells or tissues.

The cancer cell-specific antibody thus selected can then be purified further.

The method for producing a cancer microenvironment-targeting anti-podocalyxin antibody according to the present invention includes, after primary screening, a step of comparing the reactivity of the antibody with abnormal blood vessels and reactivity with normal blood vessels.

The "step of comparing the reactivity of the antibody with abnormal blood vessels and reactivity with normal blood vessels" in the present specification means a step of staining cancer cells or tissues and the antibody obtained by the primary screening by immunohistochemistry and detecting presence or absence of a bond in abnormal blood vessels, while staining normal cells or tissues and the antibody obtained by the primary screening by immunohistochemistry and studying the presence or absence of a bond in normal blood vessels.

The antibody found to have dominantly higher reactivity with abnormal blood vessels than reactivity with normal blood vessels is selected as a result of comparison between the reactivity of the antibody with abnormal blood vessels and reactivity with normal blood vessels by immunohistochemistry. In the production method of the present invention, it is more preferred to select an antibody reacting with abnormal blood vessels but not reacting with normal blood vessels.

The cancer microenvironment-targeting antibody thus selected may then be purified further.

Abnormal blood vessels occur by angiogenesis. Angiogenesis is a physiological phenomenon in which new blood vessel branches extend from an existing blood vessel and construct a vascular network. In a broad sense, angiogenesis embraces vasculogenesis in which new blood vessels are formed during embryonic development, but in a strict sense, angiogenesis is distinguished from vasculogenesis. Angiogenesis is known to occur even in a wound healing procedure and angiogenesis plays an important role also in chronic inflammation.

In the present specification, blood vessels generated by angiogenesis in a cancer microenvironment are defined as abnormal blood vessels. Every blood vessel needs supply of a nutrient from blood vessels so that abnormal blood vessels exist in every cancer.

The term "normal blood vessels" means blood vessels other than the blood vessels generated by angiogenesis in a cancer microenvironment. Angiogenesis occurs also in inflammation or during healing of wound, but blood vessels formed by it are classified into normal blood vessels in the present specification.

As the abnormal blood vessels, blood vessels present in the above-described cancer cells or tissues can be used, while as the normal blood vessels, blood vessels present in the normal cells or tissues can be used.

The cancer microenvironment-targeting anti-podocalyxin antibody of the present invention can also be produced by screening, by immunohistochemistry, a cancer cell-specific anti-podocalyxin antibody obtained by the method described below.

The cancer cell-specific anti-podocalyxin monoclonal antibody can be obtained by isolating antibody producing cells from a non-human mammal immunized with the cancer cell-specific podocalyxin or a portion thereof, fusing them with myeloma cells or the like to obtain a hybridoma, and purifying an antibody produced by the hybridoma. The cancer cell-specific anti-podocalyxin polyclonal antibody can be obtained from the serum of an animal immunized with the cancer cell-specific podocalyxin or a fragment thereof.

When the cancer microenvironment-targeting anti-podocalyxin antibody of the present invention is produced using genetic recombination, it may be produced, for example, by transforming a proper host with an expression vector containing the nucleic acid of the present invention, culturing the resulting transformant under appropriate conditions to express an antibody, and then isolating and purifying the antibody by a known method.

Examples of the isolating and purifying method include an affinity column using protein A/G/L or the like, another chromatography column, a filter, ultrafiltration, salting-out, and dialysis. These methods may be used in combination as needed.

An antibody that binds to a predetermined epitope sequence can be prepared using a method known to those skilled in the art or a method based thereon. For example, a peptide containing an epitope sequence is fixed to a solid phase carrier and a bond between the peptide and a plurality of antibodies is detected to obtain an antibody that specifically binds to the epitope.

As the "plurality of antibodies", antibodies obtained by immunizing an animal with an antigen protein or a partial peptide thereof may be used or an antibody library or an antibody fragment library constructed by phage display may be used. When a library constructed by phage display is used, it is also possible to fix a peptide containing an epitope sequence to a solid phase carrier, repeat panning, and thereby obtain an antibody that specifically binds to the epitope.

A human chimeric antibody and a human CDR grafted antibody can be prepared by cloning an antibody gene from mRNA of a hybridoma producing an antibody of an animal other than human and linking it to a portion of a human antibody gene by using genetic recombination technology.

For example, for the preparation of a human chimeric antibody, cDNA is synthesized from mRNA of a hybridoma that produces a mouse antibody by using reverse transcriptase, a heavy chain variable region (VH) and a light chain variable region (LH) are cloned by PCR, and then the sequence is analyzed. Next, a 5' primer containing a leader sequence is prepared from an antibody base sequence having a high identity and then a portion of the cDNA from the signal sequence to the 3' end of the variable region is cloned by PCR using the 5' primer and the variable region 3' primer. On the other hand, the constant region of a heavy chain and a light chain of human $IgG_1$ is cloned and for the heavy chain and the light chain, the mouse antibody-derived variable region and the human antibody-derived constant region are linked to each other by Overlapping Hanging using PCR and amplified. The DNA thus obtained is inserted into an appropriate expression vector, followed by transformation to obtain a human chimeric antibody.

For the preparation of a CDR grafted antibody, a human antibody variable region having the highest homology with a mouse antibody variable region to be used is selected and cloned and the base sequence of CDR is modified by site-selective mutagenesis using a mega-primer method. When humanization of an amino acid sequence constituting a framework region disturbs specific binding to an antigen, an amino acid of a portion of the framework may be converted from a human type to a rat type.

A CDR having an original amino acid sequence but including deletion, substitution or addition of from one to several, preferably one or two amino acids or a CDR composed of an amino acid sequence having 80% or more identity to the original sequence may be prepared using a known method such as site-specific mutagenesis, random mutagenesis, chain shuffling, or CDR walking.

It is well known to those skilled in the art that according to these methods, a CDR having more mature affinity can be obtained by displaying an antibody or antibody fragment having a variety of mutations in CDR on the phage surface by phage display and screening using an antigen (for example, Wu et al., PNAS. 1998; 95: 6037-6042.; Schier R et al., J. Mol. Bio. 1996; 263: 551-567.; Schier R et al., J. Mol. Biol. 1996; 255: 28-43.; Yang W P et al., J. Mol. Biol. 1995; 254: 392-403). The present invention also embraces an antibody containing a CDR matured in such a manner.

The antigen-binding fragment of the cancer microenvironment-targeting anti-podocalyxin antibody according to the present invention may be expressed by the above-described method using a DNA encoding the fragment. Alternatively, a full-length antibody is obtained and then treated with an enzyme such as papain or pepsin to fragment it.

The cancer microenvironment-targeting anti-podocalyxin antibody according to the present invention may be different in amino acid sequence, molecular weight, isoelectric point, presence/absence of sugar chains, conformation or the like, depending on the preparation method or purification method. However, the antibody thus obtained is encompassed in the present invention insofar as it has a similar function as a cancer microenvironment-targeting anti-podocalyxin antibody. For example, the cancer microenvironment-targeting anti-podocalyxin antibody of the present invention is obtained by expression in prokaryotic cells such as E. coli, it has a methionine residue added at the N terminal of the amino acid sequence of the original antibody. The present invention also embraces such an antibody.

When as the cancer microenvironment-targeting anti-podocalyxin antibody of the present invention, an antibody having an N-linked sugar chain having no fucose bound to N-acetylglucosamine at the reducing end is produced, it can be produced by a known method or a method based thereon. Such a method for producing an antibody is described in, for example, the pamphlet of WO2002/031140 or Japanese Patent Application Publication No. 2009-225781.

Specifically, for example, the intended cancer microenvironment-targeting anti-podocalyxin antibody can be obtained by transforming cells, whose enzymatic activity involved in the synthesis of GDP-fucose or α-1,6-fucosyltransferase activity has been reduced or deleted, by using an expression vector containing a DNA encoding the cancer microenvironment-targeting anti-podocalyxin antibody of the present invention, culturing the transformant thus obtained, and then purifying it.

Examples of the enzyme involved in synthesis of GDP-fucose include GDP-mannose 4,6-dehydratase (GMP), GDP-keto-6-deoxymannose 3,5-epimerase, 4-reductase (Fx), and GDP-beta-L-fucose pyrophosphorylase (GFPP).

Here, the cells are not particularly limited, but are preferably mammalian cells. For example, CHO cells having the above-described enzymatic activity reduced or deleted may be used.

Although the antibody composition obtained by the above method may contain an antibody having fucose bound to N-acetylglucosamine at the reducing end, a proportion of the fucose-bound antibody is 20 wt % or less, preferably 10 wt % or less, more preferably 5 wt % or less, most preferably 3 wt % or less, each based on the total weight of the antibody.

Further, the antibody having an N-linked sugar chain having no fucose bound to N-acetylglucosamine at the reducing end may also be obtained by introducing an expression vector containing a DNA encoding the cancer microenvironment-targeting anti-podocalyxin antibody of the present invention into insect eggs, hatching and growing the insects, and crossbreeding them if necessary to produce a transgenic insect, and extracting the cancer microenvironment-targeting anti-podocalyxin antibody from the transgenic insect or a secretion thereof. As the insect, a silkworm may be used. In this case, the antibody can be extracted from a silkworm cocoon.

Although the antibody composition obtained using the above method may also contain an antibody having fucose bound to N-acetylglucosamine at the reducing end, a proportion of the fucose-bound antibody is 20 wt % or less, preferably 10 wt % or less, more preferably 5 wt % or less, most preferably 3 wt % or less, each based on the total weight of the antibody.

(Activity of Cancer Microenvironment-Targeting Anti-Podocalyxin Antibody of the Present Invention)

The drug efficacy mechanism of an antibody drug is based on two biological activities of the antibody. One of them is a target antigen-specific binding activity, which is an activity neutralizing the function of a target antigen molecule through binding thereto. Functional neutralization of the target antigen molecule is exhibited via the Fab region.

The other one is a biological activity of an antibody called "effector activity". The effector activity is exhibited as a mode such as antibody-dependent cellular cytotoxicity (ADCC), complement-dependent cytotoxicity (CDC), or direct induction of apoptosis via the Fc region of the antibody.

The activities of the cancer microenvironment-targeting anti-podocalyxin antibody of the present invention can be measured in the following methods.

(1) Binding Activity

The binding activity of an antibody can be measured by a known method, for example, enzyme-linked immunosorbent assay (ELISA), enzyme immunoassay (EIA), radioimmunoassay (RIA), a fluorescent antibody method, or an FACS method.

(2) ADCC Activity

The term "ADCC activity" means a target cell damaging activity and it is achieved by binding, when the antibody of the present invention binds to the cell surface antigen of target cells, Fcγ receptor-bearing cells (effector cells) to the Fc portion via a Fcγ receptor.

The ADCC activity can be known by mixing target cells in which podocalyxin is expressed, effector cells, and the cancer microenvironment-targeting anti-podocalyxin antibody of the present invention, and measuring the degree of ADCC. As the effector cells, for example, mouse splenocytes, or monocytes isolated from the human peripheral blood or bone marrow can be used. As the target cells, for example, podocalyxin-positive cancer cells can be used. The activity can be measured by labeling target cells with $^{51}$Cr or the like in advance, adding the antibody of the present invention to the resulting cells, incubating the resulting mixture, adding effector cells to the target cells at a ratio adequate therefor, incubating the resulting mixture, collecting the supernatant, and then counting the label in the supernatant.

(3) CDC Activity

The term "CDC activity" means cellular cytotoxicity caused by a complement system.

The CDC activity can be measured by using, in the ADCC activity test, a complement instead of the effector cells.

(4) Tumor Growth Inhibitory Activity

The tumor growth inhibitory activity can be measured using a tumor model animal. For example, a tumor is subcutaneously implanted into a mouse and the cancer microenvironment-targeting anti-podocalyxin antibody of the present invention is administered thereto. A tumor growth inhibitory effect can be measured by comparing the volume of the tumor tissue between a non-administered group and an administered group.

The tumor growth inhibitory activity may result from inhibition of growth of individual cells or may result from induction of apoptosis.

(Pharmaceutical Composition)

The cancer microenvironment-targeting anti-podocalyxin antibody or antigen-binding fragment thereof according to the present invention may be used for prevention or treatment of a cancer that expresses podocalyxin. A pharmaceutical composition according to one aspect of the present invention contains the cancer microenvironment-targeting anti-podocalyxin antibody or antigen-binding fragment thereof according to the present invention as an active ingredient and further contains a pharmacologically acceptable carrier or additive.

The cancer microenvironment-targeting anti-podocalyxin antibody or antigen-binding fragment thereof according to the present invention may be used for delivery of a drug targeting cancer cells. A pharmaceutical composition according to another aspect of the present invention contains the cancer microenvironment-targeting anti-podocalyxin antibody or antigen-binding fragment thereof to which the above-described substance having an anti-cancer activity or another anti-cancer agent has been bound and it further contains a pharmacologically acceptable carrier or additive.

Examples of the carrier and additive include, but are not limited to, water, saline, phosphate buffer, dextrose, pharmaceutically acceptable organic solvents such as glycerol and ethanol, collagen, polyvinyl alcohol, polyvinylpyrrolidone, carboxy vinyl polymers, carboxymethylcellulose sodium, sodium polyacrylate, sodium alginate, water-soluble dextran, sodium carboxymethyl starch, pectin, methylcellulose, ethylcellulose, xanthan gum, gum arabic, casein, agar, polyethylene glycol, diglycerin, glycerin, propylene glycol, petrolatum, paraffin, stearyl alcohol, stearic acid, human serum albumin, mannitol, sorbitol, lactose, and surfactants.

The pharmaceutical composition of the present invention may be provided in a variety of forms such as a solution (for example, an injection), a dispersion, a suspension, a tablet, a pill, a powder, or a suppository. A preferred aspect is an injection and parenteral (for example, intravenous, transdermal, intraperitoneal, or intramuscular) administration is preferred.

The pharmaceutical composition according to the present invention is effective for the treatment of podocalyxin-related diseases, in particular, cancer.

Examples of the podocalyxin-related cancer include, but not limited to, cerebral tumor, prostate cancer, testicular tumor, kidney cancer, thyroid gland cancer, bladder cancer, breast cancer, ovarian cancer, colorectal cancer, pancreatic cancer, malignant mesothelioma, and osteosarcoma. The cancer microenvironment-targeting anti-podocalyxin antibody according to the present invention is particularly useful for these cancers.

The pharmaceutical composition according to the present invention can also be used as a drug delivery agent for the above-described cancers.

The present invention also embraces a method of treating a podocalyxin-related disease, including administering a therapeutically effective amount of the cancer microenvironment-targeting anti-podocalyxin antibody or antigen-binding fragment thereof according to the present invention.

The term "therapeutically effective amount" as used herein means an amount of an active substance capable of alleviating one or more symptoms of a disease to be treated to a certain extent. For an anti-cancer agent, it means an amount that causes at least one of reduction of a tumor size, inhibition (retardation or stopping) of tumor metastasis, inhibition (retardation or stopping) of tumor growth, and alleviation of one or more symptoms associated with cancer.

Specifically, the dose of the cancer microenvironment-targeting anti-podocalyxin antibody or antigen-binding fragment thereof according to the present invention may be, for example, from 0.025 to 50 mg/kg, preferably from 0.1 to 50 mg/kg, more preferably from 0.1 to 25 mg/kg, still more preferably from 0.1 to 10 mg/kg or from 0.1 to 3 mg/kg, but is not limited thereto.

(Testing Method, Test Drug, Testing Kit)

As described above, podocalyxin is highly expressed in specific cancer cells. The cancer microenvironment-targeting anti-podocalyxin antibody according to the present invention is therefore useful for the diagnosis of a cancer in which podocalyxin is highly expressed such as cerebral tumor, prostate cancer, testicular tumor, kidney cancer, thyroid gland cancer, bladder cancer, breast cancer, ovarian cancer, colorectal cancer, pancreatic cancer, malignant mesothelioma, or osteosarcoma. The cancer microenvironment-targeting anti-podocalyxin antibody according to the present invention selectively binds to abnormal blood vessels so that it is particularly useful for the diagnosis.

The present invention also embraces a test drug of cancer containing the cancer microenvironment-targeting anti-podocalyxin antibody of the present invention, use of the antibody for testing of cancer, and a testing method of cancer using the cancer microenvironment-targeting anti-podocalyxin antibody of the present invention.

When the cancer microenvironment-targeting anti-podocalyxin antibody of the present invention is used in the testing method of cancer, a sample used for the test can be, for example, the tissue, serum, spinal fluid, urine, or body fluid (such as saliva or sweat) collected from a subject and suspected to have cancer. Podocalyxin is a membrane protein and is known to be secreted in the serum.

Examples of the testing method include, but are not limited to, immunoassay, aggregation method, turbidimetric method, Western blotting method, and surface plasmon resonance (SPR) method.

Of these, preferred is immunoassay that makes use of an antigen antibody reaction between the cancer microenvironment-targeting anti-podocalyxin antibody of the present invention which has been detectably labeled and cancer microenvironment-targeting podocalyxin in the sample and thereby determines the amount of the cancer microenvironment-targeting podocalyxin.

For the immunoassay, used is a detectably-labeled cancer microenvironment-targeting anti-podocalyxin antibody or an antibody (secondary antibody) against the detectably-labeled cancer microenvironment-targeting anti-podocalyxin antibody. It is classified, by an antibody labeling method, into enzyme immunoassay (EIA or ELISA), radio-immunoassay (RIA), fluorescence immunoassay (FIA), fluorescence polarization immunoassay (FPIA), chemiluminescence immunoassay (CLIA), and the like and any of them is usable in the method of the present invention.

In ELISA, an antibody labeled with an enzyme such as peroxidase or alkaline phosphatase is used: in RIA, that labeled with a radioactive substance such as $^{125}$I, $^{131}$I, $^{35}$S, or $^3$H is used; in FPIA, that labeled with a fluorescent substance such as fluorescein isothiocyanate, rhodamine, dansyl chloride, phycoerythrin, tetramethylrhodamine isothiocyanate, or near-infrared fluorescent material is used; and in CLIA, that labeled with a luminescent substance such as luciferase, luciferin, or aequorin is used. In addition, an antibody labeled with nanoparticles such as colloidal gold or quantum dot can be detected.

In immunoassay, detection may also be carried out by labeling the cancer microenvironment-targeting anti-podocalyxin antibody with biotin and then binding avidin or streptavidin labeled with an enzyme or the like to the antibody.

Among immunoassays, ELISA using enzyme labeling is preferred because the amount of an antigen can be measured conveniently and speedily.

ELISA has competitive assay and sandwich assay. In the competitive assay, the cancer microenvironment-targeting anti-podocalyxin antibody is immobilized onto a solid phase support such as microplate and then the sample and the enzyme-labeled cancer-specific podocalyxin are added to cause an antigen antibody reaction. After washing, the reaction product is reacted with an enzyme substrate to cause color development and an absorbance is measured. The sample containing a larger amount of podocalyxin shows weaker color development, while that containing a smaller amount of podocalyxin shows stronger color development so that the podocalyxin amount can be determined using a calibration curve.

In the sandwich assay, after the cancer microenvironment-targeting anti-podocalyxin antibody is fixed onto a solid phase support and the sample is added to cause a reaction therebetween, an enzyme-labeled cancer microenvironment-targeting anti-podocalyxin antibody capable of recognizing another epitope is added further to cause a reaction therebetween. After washing, reaction with an enzyme substrate, and color development, an absorbance is measured to determine a podocalyxin amount. Alternatively, in the sandwich assay, it is also possible to, after reaction between the cancer microenvironment-targeting anti-podocalyxin antibody immobilized onto a solid phase support and cancer-specific podocalyxin in the sample, add a non-labeled antibody (primary antibody), and add an antibody (secondary antibody) against this non-labeled antibody after labeling with an enzyme.

When the enzyme is a peroxidase, 3,3'-diaminobenzidine (DAB), 3,3'5,5'-tetramethylbenzidine (TMB), or o-phenylenediamine (OPD) can be used as the enzyme substrate. When the enzyme is an alkaline phosphatase, p-nitropheny phosphate (NPP) or the like can be used.

In the present specification, the "solid phase support" is not particularly limited insofar as it permits fixing of an antibody thereonto. Examples include microtiter plates, substrates, beads made of glass, a metal, a resin, or the like, nitrocellulose membranes, nylon membranes, and PVDF membranes. The target substance can be fixed onto such a solid phase support in a known manner.

In the above immunoassay, an aggregation method is also preferred as a method capable of conveniently detecting a trace amount of a protein. Examples of the aggregation method include a latex aggregation method performed by binding latex particles to an antibody.

When the cancer microenvironment-targeting anti-podocalyxin antibody is bound to latex particles and mixed with the sample, the antibody-bound latex particles aggregate in the presence of cancer-specific podocalyxin. The concentration of the antigen can therefore be determined by exposing the sample to a near infrared light and quantitatively determining the resulting aggregated mass by measurement of absorbance (turbidimetry) or measurement of a scattered light (nephelometry).

The term "testing" as used herein means analyzing a sample collected from a subject in order to obtain data necessary for diagnosis. The testing method of the present invention can be performed, for example, by a test company.

The testing method in one aspect of the present invention includes a step of analyzing whether a cancer-specific podocalyxin amount in the sample of a subject is larger than a cancer-specific podocalyxin amount of a non-cancer patient. When the cancer-specific podocalyxin amount in the sample of a subject is significantly larger than that of the sample of a non-cancer patient, it is judged that the subject suffers from a cancer with high possibility.

The testing method in another aspect of the present invention includes a step of measuring, with the passage of time, a cancer-specific podocalyxin amount in the sample of a patient subjected to cancer treatment and analyzing variation in the cancer-specific podocalyxin amount. When the podocalyxin amount tends to increase with the passage of time, it is judged that the patient has recurrence or metastasis of cancer with high possibility.

The present invention also embraces a diagnostic agent of cancer containing the cancer microenvironment-targeting anti-podocalyxin antibody of the present invention, use of the cancer microenvironment-targeting anti-podocalyxin antibody of the present invention for the diagnosis of cancer, and a diagnostic method of cancer using the cancer microenvironment-targeting anti-podocalyxin antibody of the present invention. The term "diagnosis" as used herein means that persons involved in medical practice such as doctors judge the possibility of a subject suffering from cancer or the possibility of recurrence and metastasis of cancer.

[Testing Kit of Cancer]

A testing kit of cancer according to the present invention is a kit for testing a cancer by using the above-described testing method and it includes the cancer microenvironment-targeting anti-podocalyxin antibody.

The testing kit according to the present invention includes a reagent, apparatus, and the like necessary for measuring a podocalyxin amount by immunoassay making use of an antigen antibody reaction between the cancer microenvironment-targeting anti-podocalyxin antibody and cancer-specific podocalyxin.

In one aspect, a testing kit is for measuring the amount of cancer-specific podocalyxin by sandwich assay and it includes a microtiter plate, a cancer microenvironment-targeting anti-podocalyxin antibody for capturing, a cancer microenvironment-targeting anti-podocalyxin antibody labeled with an alkaline phosphatase or peroxidase; and an alkaline phosphatase substrate (NPP, or the like) or a peroxidase substrate (DAB, TMB, OPD, etc.).

The capturing antibody and the labeled antibody recognize respectively different epitopes.

In such a kit, first, the capturing antibody is fixed onto the microtiter plate. A sample diluted as needed is then added to the microtiter plate, followed by incubation, removal of the sample, and washing. After addition of the labeled antibody and incubation, the substrate is added to cause color development. The amount of cancer-specific podocalyxin can then be determined by analyzing the color development by means of a microtiter plate reader or the like.

In another aspect, the testing kit is for measuring the amount of cancer-specific podocalyxin by sandwich assay while using a secondary antibody. It includes a microtiter plate, a cancer microenvironment-targeting anti-podocalyxin antibody for capturing, a cancer microenvironment-targeting anti-podocalyxin antibody serving as a primary antibody, a cancer microenvironment-targeting anti-podocalyxin antibody labeled with an alkaline phosphatase or peroxidase, serving as a secondary antibody; and an alkaline phosphatase substrate (NPP, or the like) or a peroxidase substrate (DAB, TMB, OPD, etc.).

The capturing antibody and the primary antibody recognize respectively different epitopes.

In such a kit, first, the capturing antibody is fixed onto the microtiter plate. A sample diluted as needed is then added to the resulting microtiter plate, followed by incubation, removal of the sample, and washing. After addition of the primary antibody, incubation and washing are carried out. Further, the enzyme-labeled secondary antibody is added. After incubation, the substrate is added to cause color development. The amount of cancer-specific podocalyxin can then be determined by analyzing the color development by using a microtiter plate reader or the like. Using the secondary antibody can amplify the reaction and enhance the detection sensitivity.

In a further aspect, the testing kit includes a microtiter plate, a cancer microenvironment-targeting anti-podocalyxin antibody serving as a primary antibody, a cancer microenvironment-targeting anti-podocalyxin antibody labeled with an alkaline phosphatase or peroxidase; and an alkaline phosphatase substrate or a peroxidase substrate.

In such a kit, first, the microtiter plate is coated with a sample diluted to a proper concentration, followed by the addition of the primary antibody. After incubation and washing, the enzyme-labeled secondary antibody is added, followed by incubation and washing. Then, the substrate is added to cause color development.

The amount of cancer-specific podocalyxin can be determined by analyzing color development by using a microtiter plate reader or the like.

It is preferred that each testing kit further includes a buffer, an enzymatic reaction stop solution, a microtiter plate reader, or the like necessary for testing.

The labeled antibody is not limited to an enzyme-labeled antibody and it may be an antibody labeled with a radioactive substance (such as $^{25}I$, $^{131}I$, $^{35}S$, or $^{3}H$), a fluorescent substance (such as fluorescein isothiocyanate, rhodamine, dansyl chloride, phycoerythrin, tetramethylrhodamine isothiocyanate, or near-infrared fluorescent material), a luminescent substance (such as luciferase, luciferin, or aequorin), nanoparticles (colloidal gold or quantum dot) or the like. In addition, it is also possible to use a biotinylated antibody as the labeled antibody and add labeled avidin or streptavidin to the kit.

In a still further aspect, the testing kit of the present invention is for measuring the amount of cancer-specific podocalyxin by the latex aggregation method. This kit includes latex sensitized with the cancer microenvironment-targeting anti-podocalyxin antibody. After the sample is mixed with the cancer microenvironment-targeting anti-podocalyxin antibody, the aggregated mass is quantitatively determined by an optical method. The kit preferably includes, in addition, an aggregation reaction plate that visualizes the aggregation reaction.

The testing kit according to the present invention can also be used as a diagnostic kit. For the testing method and diagnostic method of cancer and the testing kit and diagnostic kit of cancer according to the present invention, the cancer microenvironment-targeting anti-podocalyxin antibody of the present invention may be replaced by the antigen-binding fragment thereof.

All the disclosed patent documents and non-patent documents to be cited herein are incorporated herein as an entirety by reference.

Examples

The present invention will hereinafter be described specifically based on embodiments. The present invention is not limited to or by them. Those skilled in the art can change the present invention into various aspects without departing from the gist of the present invention. Such a change is also encompassed within the scope of the present invention.

1. Preparation of Anti-Podocalyxin Antibody

A stable expression line (LN229/sol-hPODXL) of secretory type human podocalyxin was established by introducing, by the lipofection method (of Life Technologies), the extracellular region (from $26^{th}$ to $426^{th}$ amino acids in SEQ ID NO: 1) of human podocalyxin into LN229 cells of a human glioblastoma cell line (purchased from ATCC) and performing drug selection by using G418 (product of Life Technologies). To the C terminus of the secretory type human podocalyxin was added PA tag (Fujii Y et al., Protein Expr Purif. 2014; 95: 240-247.) developed by the present inventors. The LN229/sol-hPODXL thus obtained was mass cultured on a DMEM medium (product of Wako Pure Chemical Industries) containing a 10% fetal bovine serum (FBS; product of Life Technologies) and the supernatant was collected. The supernatant thus collected was filtered through a 0.22 μm-filter (product of Millipore) and the secretory type podocalyxin was purified using a PA tag system. For elution of the secretory type podocalyxin, 0.1 mg/mL of PA tag peptide (hpp4051: peptide having 12 amino acids) was used. The absorbance at OD280 was measured using NanoDrop Lite (product of Thermo Scientific).

Balb/c mice (female, 4 week old; product of CLEA Japan) were immunized with the purified secretory type podocalyxin according to the following schedule.

As the first immunization, a mixture of 100 μg of the secretory type podocalyxin suspended in 0.5 mL of PBS with 0.5 mL of ImjectAlum (product of Thermo Scientific) as an adjuvant was intraperitoneally administered.

As the second immunization, a suspension obtained by suspending 100 μg of the secretory type podocalyxin and $1 \times 10^7$ cells of LN229/hPODXL in 0.5 mL of PBS was intraperitoneally administered.

As the third to fifth immunization, a suspension obtained by suspending $1 \times 10^7$ cells of LN229/hPODXL in 0.5 mL of PBS was intraperitoneally administered.

Forty eight hours after the final immunization, the spleen was taken out from the immunized mice and spleen cells were extracted. The spleen cells were fused with mouse myeloma P3U1 cells (purchased from ATCC) by using polyethylene glycol 1,500 (product of Sigma Aldrich). The fused product was cultured for 10 days on a 10% FBS/RPMI medium (product of Wako Pure Chemical Industries) containing hypoxanthine, aminopterin and thymidine (HAT; product of Life Technologies). The secreted antibody was subjected to primary screening by ELISA.

As the antigen for ELISA, the secretory type human podocalyxin was immobilized. The secretory type human podocalyxin (1 μg/mL) was immobilized onto MaxiSorp (product of Thermo Scientific) and blocking was performed with 1% BSA/PBS. The hybridoma culture supernatant was used as a primary antibody liquid, while anti-mouse IgG-HRP (product of Dako) was used as a secondary antibody liquid. All the antigen antibody reactions were performed at room temperature and the plate was washed with PBS containing 0.05% Tween-20. For detection, 1-Step Ultra TMB-ELISA (product of Thermo Scientific) was used and absorbance at 655 nm was measured using a microplate reader (product of Bio-rad).

2. Flow Cytometry

For secondary screening, LN229 cells having endogenously expressed human podocalyxin and cells obtained by forcibly expressing human podocalyxin in LN229 cells (podocalyxin forcibly-expressed LN229 cells) were used and reactivity was investigated. The monoclonal antibody established was evaluated using the LN229 cells, the podocalyxin forcibly-expressed LN229 cells, and a vascular endothelial cell line (purchased from Cambrex). Per reaction, $1 \times 10^5$ cells were used. The culture supernatant was added to the cells and a primary antibody reaction was performed for one hour on ice. After washing with 0.1% BSA/PBS, an Alexa488-labeled anti-mouse IgG antibody (1/1,000 dilution, product of Thermo Scientific) was added and a secondary antibody reaction was performed for 30 minutes on ice. After washing with 0.1% BSA/PBS, analysis was performed using Cell Analyzer EC800 (product of Sony).

A primary antibody reacting with the podocalyxin forcibly-expressed LN229 cells but not reacting with the vascular endothelial cells was established.

3. Immunohistochemistry

Paraffin sections of breast cancer tissues and normal tissues (human kidney, human small intestine) were deparaffinized through xylene and ethanol series. Antigen activation was then performed with a citrate buffer having pH 6.0 (product of Dako) by an autoclave. Endogenous peroxidase was inactivated with 3% $H_2O_2$. After blocking with SuperBlock (product of Thermo Fisher) at room temperature for 10 minutes, the primary antibody was reacted at a concentration of 1 μg/mL at room temperature for one hour. After amplification using Envision+ (product of Dako), color was developed using DAB (product of Dako). In the clone (PcMab-60) thus established, none of the normal blood vessels and the glomeruli of the kidney and the normal blood vessels of the small intestine were stained and the abnormal blood vessels around the cancer cells of the breast cancer tissues were stained.

4. Determination of Amino Acid Sequence and Base Sequence of PcMab-60

From $1 \times 10^6$ PcMab-60 hybridoma cells, a total RNA was extracted using a QIAGEN RNeasy mini kit. cDNA synthesis was performed using 5 of the total RNA by a SuperScript III First-Strand Syntheses kit. The cDNA was used as a template in the following experiment.

In order to prepare human chimera type PcMab-60 (chPcMab-60), a DNA encoding the VH region of PcMab-60 was amplified using PCR and inserted in a pCAG vector retaining a DNA encoding the CH1, hinge region, CH2, and CH3 regions of human IgG$_1$ (pCAG-hIgG$_1$hG2b/PcMab-60HVH (G418)). In addition, a DNA encoding the VL region of PcMab-60 was amplified using PCR and inserted in a pCAG vector (pCAG/PcMab-60L (zeocin)).

For amplification of the heavy chain, the following primers were used:

```
InFs.HindIII-Pc60H:
                                      (SEQ ID NO: 12)
CGGTATCGATAAGCTTCCAATGTCCTCTCCACAG InFr.Pc60HVH-BamHI:
                                      (SEQ ID NO: 13)
GGCCCTTGGTGGATCCGACGGTGACTGAGGTTC
```

The PCR reaction was performed using QIAGEN HotStar HiFidelity DNA polymerase. The reaction was made under the following temperature conditions: first at 95° C. for 5 minutes, next 35 cycles of 94° C. for 15 seconds, 50° C. for 1 minute, and 72° C. for 1 minute, and lastly 72° C. for 10 minutes. The amplified PCR product was purified using FastGene Gel/PCR Extraction. The heavy chain PCR product of PcMab-60 enzymatically treated with restriction enzymes HindIII and NotI was subcloned by the InFusion method into a pCAG-hIgG$_1$hG2b vector (G418) purified by a Fast-Gene Gel/PCR Extraction kit and the base sequence was determined from the vector primer.

For amplification of the light chain, the following primers were used.

```
InFs.HindIII-Pc60L:
                                      (SEQ ID NO: 14)
CGGTATCGATAAGCTTAAAATGATGAGTCCTGCCC InF.mIgCKterNotI:
                                      (SEQ ID NO: 15)
TCTAGAGTCGCGGCCGCCTAACACTCATTCCTGT
```

The PCR reaction was performed using QIAGEN HotStar HiFidelity DNA polymerase. The reaction was made under the following temperature conditions: first at 95° C. for 5 minutes, next 35 cycles of 94° C. for 15 seconds, 50° C. for 1 minute, and 72° C. for 1 minute, and lastly 72° C. for 10 minutes. The amplified PCR product was purified using FastGene Gel/PCR Extraction. The light chain PCR product of PcMab-60 enzymatically treated with restriction enzymes HindIII and NotI was subcloned by the InFusion method into a pCAG vector (zeocin) purified by a FastGene Gel/PCR Extraction kit and the base sequence was determined from the vector primer.

The base sequence of the DNA encoding the heavy chain of chPcMab-60 was as shown in SEQ ID NO: 11 and the base sequence of the DNA encoding the light chain of PcMab-60 was as shown in SEQ ID NO: 9.

The amino acid sequence was predicted from the base sequence.

The heavy chain amino acid sequence of chPcMab-60 was as shown in SEQ ID NO: 10 and the light chain amino acid sequence of PcMab-60 was as shown in SEQ ID NO: 8.

5. Determination of CDR

The site of CDR was specified from the resulting base sequence by using a sequence prediction soft of immunoglobulin provided on the home page (abYsis) of the following URL.
(HyperTextTransferProtocol://WorldWideWeb.bioinf.org.uk/abysis/sequ ence_input/key_annotation/key_annotation.HyperTextMarkupLanguage, wherein "HyperTextTransferProtocol" is "http", "WorldWideWeb" is "www", and "HyperTextMarkupLanguage" is "html")

The amino acid sequences of the heavy chains CDR1 to 3 and the light chains CDR1 to 3 of PcMab-60 were specified as shown in SEQ ID NOS: 2 to 7, respectively.

6. Preparation of Human Chimeric PcMab-60 (chPcMab-60)

As pCAG-hIgG$_1$hG2b/PcMab-60HVH (G418) and pCAG/PcMab-60L (zeocin), those prepared above in 4 were used.

After pCAG-hIgG$_1$hG2b/PcMab-60HVH (G418) and pCAG/PcMab-60L (zeocin), each 2.5 µg, were mixed, the resulting mixture was transfected into 5×10$^5$ CHO-S cells (corresponding to 1 well of a 6-well plate) in accordance with the method of Lipofectamin LTX. After 24 hours, selection of transfected cells was started on a medium containing 500 µg/mL of zeocin and 1 mg/mL of G418. The reactivity of the supernatant of the selected cells with the podocalyxin forcibly-expressed LN229 cells (LN229/hPODXL) was confirmed by flow cytometry.

The highly expressed line of chPcMab-60 was cultured on a serum-free medium (product of Thermo Fisher) and a culture supernatant was collected. The supernatant thus collected was filtered through a 0.22 µm filter (product of Millipore) and passed through a protein G column (product of GE Healthcare) to purify the chPcMab-60. The chPcMab-60 has a heavy chain having an amino acid sequence represented by SEQ ID NO: 10 and a light chain having an amino acid sequence represented by SEQ ID NO: 8. The base sequence of the DNA encoding the heavy chain is shown in SEQ ID NO: 11 and the base sequence of the DNA encoding the light chain is shown in SEQ ID NO: 9.

The heavy chain of the chPcMab-60 has a VH region of the PcMab-60, and CH1, a hinge region, CH2, and CH3 derived from human IgG$_1$.

7. Reactivity of Anti-Podocalyxin Antibody with Podocalyxin

Figure 2:
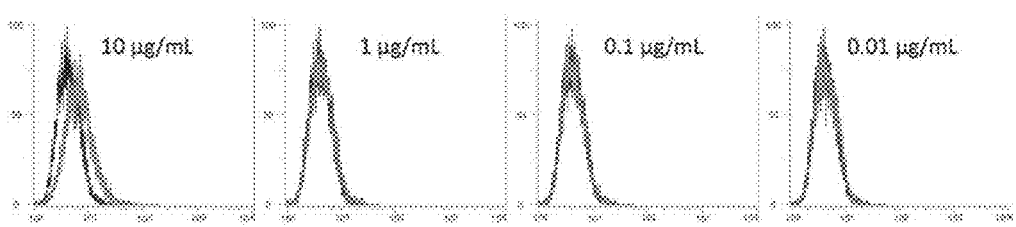
FIG. 2A shows the flow cytometry results, at each concentration, of a human chimeric PcMab-60 (chPcMab-60), that is, a cancer microenvironment-targeting anti-podocalyxin antibody, which is an antibody against podocalyxin, by using LN229.
FIG. 2B shows the flow cytometry results, at each concentration, of chPcMab-60 by using LN229/hPODXL.
Figure 2:

It was confirmed that PcMab-60 and chPcMab-60 concentration-dependently showed reactivity with podocalyxin. Used were LN229 (purchased from ATCC), human podocalyxin forcibly-expressed LN229 cells (LN229/hPODXL), and a vascular endothelial cell line (purchased from Cambrex). Per one reaction, 1×10$^5$ cells were used. The purified anti-podocalyxin antibody having a concentration of from 0.01 to 10 µg/mL was added to the cells and a primary antibody reaction was performed on ice for one hour. After washing with 0.1% BSA/PBS, a FITC-labeled anti-human IgG antibody (1/1000 dilution, product of Thermo Fisher) was added and a secondary antibody reaction was performed for 30 minutes on ice. After washing with 0.1% BSA/PBS, analysis was performed using Cell Analyzer EC800 (product of Sony). The results are shown in FIGS. 1 and 2. The results of FIGS. 1 and 2 show that the PcMab-60 and chPcMab-60 thus obtained each concentration-dependently reacted with the human podocalyxin forcibly-expressed LN229/hPODXL, though not reacting with LN229.

8. Preparation of PcMab-47

A stable expression line (LN229/sol-hPODXL) of secretory type human podocalyxin was established by introducing, by the lipofection method (product of Life Technologies), the extracellular region (from 26th to 426th amino acids in SEQ ID NO: 1) of human podocalyxin into LN229 cells of a human cerebral tumor cell line (purchased from ATCC) and performing drug selection by using G418. To the C terminus of the secretory type human podocalyxin was added PA tag (Fujii Y et al., Protein Expr Purif. 2014; 95: 240-247.) developed by the present inventors. The LN229/sol-hPODXL thus obtained was mass cultured on a DMEM medium (product of Wako Pure Chemical Industries) containing a 10% fetal bovine serum (FBS; product of Life Technologies) and the supernatant was collected. The supernatant thus collected was filtered through a 0.22 µm-filter (product of Millipore) and the secretory type podocalyxin was purified using a PA tag system. For elution of the secretory type podocalyxin, 0.1 mg/mL of PA tag peptide (hpp4051: peptide having 12 amino acids) was used. The absorbance at OD280 was measured using NanoDrop Lite (product of Thermo Scientific).

Balb/c mice (female, 5 week old; product of CLEA Japan) were immunized with the purified secretory type podocalyxin. Immunization was performed 5 times at intervals of from 7 to 14 days by intraperitoneally administering, at one time, 100 µg of it suspended in 0.5 mL of PBS. Only the first immunization was performed with a mixture of the suspension with 0.5 mL of ImjectAlum (product of Thermo Scientific) as an adjuvant. Forty eight hours after the final immunization, the spleen was taken out from the immunized mice and spleen cells were extracted. The spleen cells were fused with mouse myeloma P3U1 cells (purchased from ATCC) by using polyethylene glycol 1,500 (product of Sigma Aldrich). The fused product was cultured for 10 days on a 10% FBS/RPMI medium (product of Wako Pure Chemical Industries) containing hypoxanthine, aminopterin and thymidine (HAT; product of Life Technologies). The secreted antibody was subjected to primary screening by ELISA.

As the antigen of ELISA, the secretory type human podocalyxin was immobilized. The secretory type human podocalyxin (1 µg/mL) was immobilized onto MaxiSorp (product of Thermo Scientific) and blocking was performed with 1% BSA/PBS. The hybridoma culture supernatant was used as a primary antibody liquid, while anti-mouse IgG-HRP (product of Dako) was used as a secondary antibody liquid. All the antigen antibody reactions were performed at room temperature and the plate was washed with PBS containing 0.05% Tween-20. For detection, 1-Step Ultra TMB-ELISA (product of Thermo Scientific) was used and absorbance at 655 nm was measured using a microplate reader (product of Bio-rad).

In secondary screening, reactivity was investigated using the LN229 cells having endogenously expressed human podocalyxin and cells obtained by forced expression of human podocalyxin in the LN229 cells. The monoclonal antibody established was evaluated using, in addition to the above-described cells, a glioblastoma cell line LN229 (purchased from ATCC), a breast cancer cell line MCF-7 (purchased from ATCC), an osteosarcoma cell line U2-OS (purchased from ATCC), and a vascular endothelial cell line (purchased from Cambrex). Per one reaction, $1 \times 10^5$ cells were used. The culture supernatant was added to the cells and the primary antibody was reacted at a concentration of 10 µg/mL for one hour on ice. After washing with 0.1% BSA/PBS, an Alexa488-labeled anti-mouse IgG antibody (1/1,000 dilution, product of Life Technologies) was added and a secondary antibody reaction was performed for 30 minutes on ice. After washing with 0.1% BSA/PBS, analysis was performed using Cell Analyzer EC800 (product of Sony). A clone (PcMab-47) reacting with various cancer cell lines and vascular endothelial cells was established.

Figure 3:
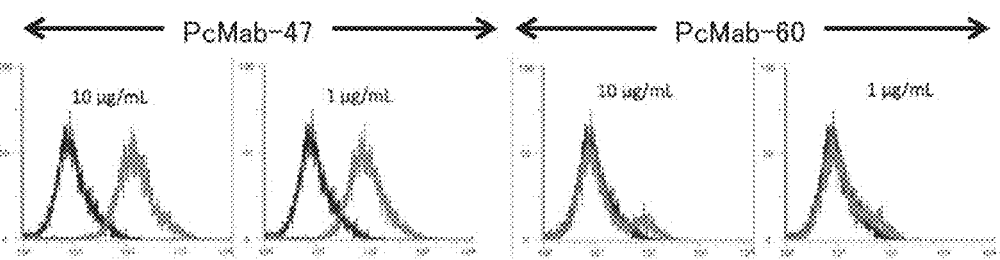
FIG. 3A and FIG. 3B show the flow cytometry results of PcMab-47 and PcMab-60, each a cancer microenvironment-targeting anti-podocalyxin antibody, which is an antibody against podocalyxin, by using two normal vascular endothelial cells, respectively.
Figure 3:
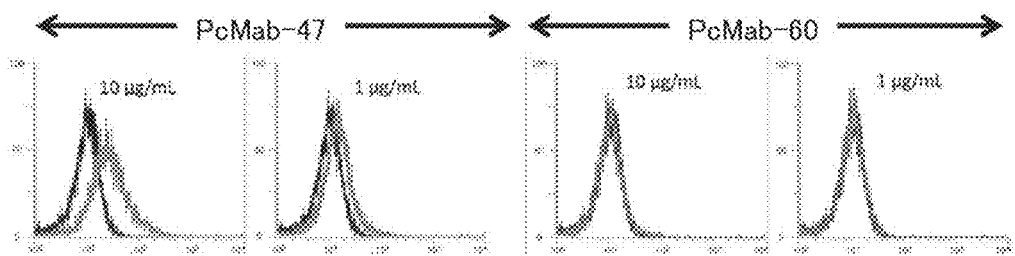

The results of flow cytometry of PcMab-47 and PcMab-60 performed using two normal vascular epithelial cells are shown in FIG. 3. PcMab-47 showed concentration-dependent reactivity with the normal vascular epithelial cells different in lot but PcMab-60 did not show reactivity with normal vascular epithelial cells. It has been confirmed from the above results that PcMab-60 is not donor specific and does not react with normal vascular epithelial cells.

Figure 4:
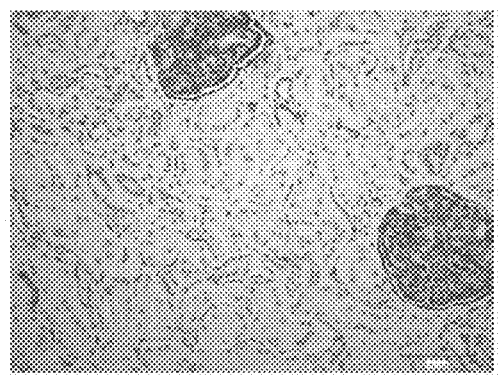
FIGS. 4A to 4D show the immunohistochemistry results of PcMab-47 and PcMab-60, each an anti-podocalyxin antibody, which is an antibody against podocalyxin, by using normal tissues.
FIG. 4E and FIG. 4F show the immunohistochemistry results of PcMab-47 and PcMab-60, each an anti-podocalyxin antibody, which is an antibody against podocalyxin, by using breast cancer tissues and the arrow in FIG. 4E
Figure 4:
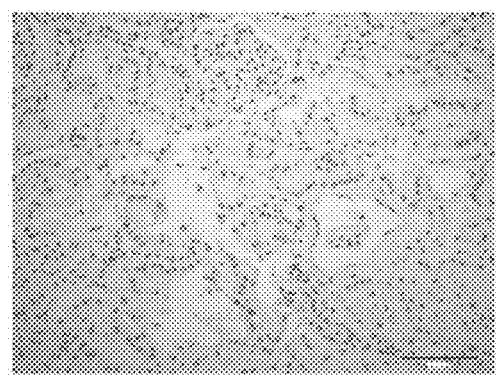
Figure 4:
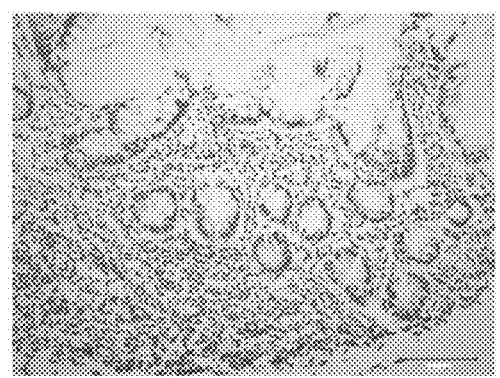
Figure 4:
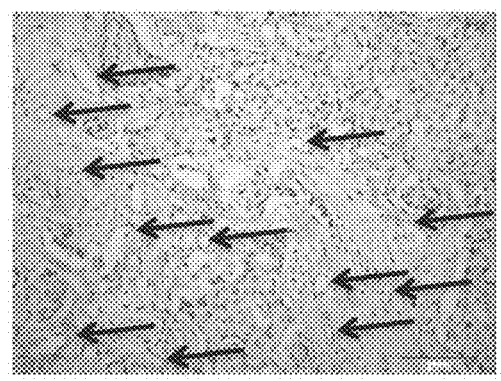

The results of immunohistochemistry of PcMab-47 and PcMab-60 performed using normal tissues and breast cancer tissues are shown in FIG. 4. It has been found from the results of FIG. 4 that PcMab-60 shows reactivity only with abnormal blood vessels in the cancer microenvironment.

Pc-Mab-47 showed good reactivity not only with podocalyxin expressed in cancer cells but also normal blood vessels or abnormal blood vessels in the cancer microenvironment. PcMab-60 prepared in Example, on the other hand, reacted with neither the normal vascular epithelial cells nor renal glomeruli but reacted only with the abnormal blood vessels observed in the microenvironment of the breast cancer tissues.

There has so far been no report on an antibody that does not react with normal blood vessels but specifically reacts only with abnormal blood vessels in the cancer microenvironment. PcMab-60 which is a novel anti-podocalyxin antibody targeting a cancer microenvironment can be established. By binding an anticancer agent or target isotope to the PcMab-60 thus obtained and administering it to cancer patients, the anticancer agent or target isotope can be brought to abnormal blood vessels in the cancer microenvironment. It is pointed out at present that a therapy targeting only cancer cells has a restrictive effect and a therapy targeting the cancer microenvironment will be an important strategy in molecular target therapy of cancer in future.

INDUSTRIAL APPLICABILITY

The cancer microenvironment-targeting anti-podocalyxin antibody of the present invention has industrial applicability as an antibody drug.

Sequence Listing Free Text

SEQ ID NO: 1 shows the amino acid sequence of human podocalyxin.

SEQ ID NOS: 2 to 4 show the respective amino acid sequences of heavy chains CDR1 to 3 of chPcMab-60.

SEQ ID NOS: 5 to 7 show the respective amino acid sequences of light chains CDR1 to 3 of PcMab-60.

SEQ ID NOS: 8 and 9 show the amino acid sequence and DNA sequence of the light chain of PcMab-60, respectively.

SEQ ID NOS: 10 and 11 show the amino acid sequence and DNA sequence of the heavy chain of chPcMab-60, respectively.

SEQ ID NO: 12 shows the DNA sequence of primer InFs.HindIII-Pc60H.

SEQ ID NO: 13 shows the DNA sequence of primer InFr.Pc60HVH-BamHI.

SEQ ID NO: 14 shows the DNA sequence of primer InFs.HindIII-Pc60L.

SEQ ID NO: 15 shows the DNA sequence of primer InF.mIgCKterNotI.

What is claimed is:

1. A cancer microenvironment-targeting anti-podocalyxin antibody or an antigen-binding fragment thereof, comprising
   a heavy chain CDR1 comprising SEQ ID NO: 2,
   a heavy chain CDR2 comprising SEQ ID NO: 3,
   a heavy chain CDR3 comprising SEQ ID NO: 4,
   a light chain CDR1 comprising SEQ ID NO: 5,
   a light chain CDR2 comprising SEQ ID NO: 6 and
   a light chain CDR3 comprising SEQ ID NO: 7.

2. The cancer microenvironment-targeting anti-podocalyxin antibody or antigen-binding fragment thereof according claim 1, wherein one or more N-linked sugar chains are bound to an Fc region and fucose is not bound to N-acetylglucosamine at a reducing end of the N-linked sugar chains.

3. A pharmaceutical composition comprising, as an active ingredient thereof, the cancer microenvironment-targeting anti-podocalyxin antibody or antigen-binding fragment thereof as claimed in claim 1.

4. A pharmaceutical composition comprising, as an active ingredient thereof, the cancer microenvironment-targeting anti-podocalyxin antibody or antigen-binding fragment thereof as claimed in claim 1 to which a substance having an anti-cancer activity has been bound.

5. A nucleic acid encoding the cancer microenvironment-targeting anti-podocalyxin antibody or antigen-binding fragment thereof as claimed in claim 1.

6. A method of treating a subject for cancer, which comprises administering to the subject the pharmaceutical composition as claimed in claim 3.

7. A method of treating a subject for cancer, which comprises administering to the subject the pharmaceutical composition as claimed in claim 4.

8. An expression vector comprising the nucleic acid as claimed in claim 5.

9. A transformant comprising the expression vector as claimed in claim 8.

10. A method of treating a subject for cancer, which comprises administering to the subject the cancer microenvironment-targeting anti-podocalyxin antibody or antigen-binding fragment thereof as claimed in claim 1.

11. The cancer microenvironment-targeting anti-podocalyxin antibody or the antigen-binding fragment according to claim 1, wherein the cancer microenvironment-targeting anti-podocalyxin antibody or antigen-binding fragment thereof comprises (1)
   a heavy chain CDR1 comprising SEQ ID NO: 2,
   a heavy chain CDR2 comprising SEQ ID NO: 3,
   a heavy chain CDR3 comprising SEQ ID NO: 4,
   a light chain CDR1 comprising SEQ ID NO: 5,
   a light chain CDR2 comprising SEQ ID NO: 6 and
   a light chain CDR3 comprising SEQ ID NO: 7 and
   (2) (a) a heavy chain having 80% or more identity with the amino acid sequence represented by SEQ ID NO: 10;
   (b) a light chain having 80% or more identity with the amino acid sequence represented by SEQ ID NO: 8, or
   (c) a heavy chain having 80% or more identity with the amino acid sequence represented by SEQ ID NO: 10 and a light chain having 80% or more identity with the amino acid sequence represented by SEQ ID NO: 8.

12. A nucleic acid encoding any one of the heavy chains and the light chains as claimed in claim 11.

13. An expression vector comprising the nucleic acid as claimed in claim 12.

14. A transformant comprising the expression vector as claimed in claim 13.

15. A pharmaceutical composition comprising, as an active ingredient thereof, the cancer microenvironment-targeting anti-podocalyxin antibody or antigen-binding fragment thereof as claimed in claim 11.

16. A method of treating a subject for cancer, which comprises administering to the subject the pharmaceutical composition as claimed in claim 15.

17. A pharmaceutical composition comprising, as an active ingredient thereof, the cancer microenvironment-targeting anti-podocalyxin antibody or antigen-binding fragment thereof as claimed in claim 11 to which a substance having an anti-cancer activity has been bound.

18. A method of treating a subject for cancer, which comprises administering to the subject the pharmaceutical composition as claimed in claim 17.

19. A method of treating a subject for cancer, which comprises administering to the subject the cancer microenvironment-targeting anti-podocalyxin antibody or antigen-binding fragment thereof as claimed in claim 11.

* * * * *

UNITED STATES PATENT AND TRADEMARK OFFICE
CERTIFICATE OF CORRECTION

PATENT NO. : 11,046,778 B2
APPLICATION NO. : 16/088941
DATED : June 29, 2021
INVENTOR(S) : Kato et al.

Page 1 of 1

It is certified that error appears in the above-identified patent and that said Letters Patent is hereby corrected as shown below:

In the Specification

Column 26, Line 57, change "5 of" to --5 μg of--.
Column 27, Line 64, change "sequ ence" to --sequence--.

Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 15

<210> SEQ ID NO 1
<211> LENGTH: 558
<212> TYPE: PRT
<213> ORGANISM: Homo sapiens

<400> SEQUENCE: 1

```
Met Arg Cys Ala Leu Ala Leu Ser Ala Leu Leu Leu Leu Leu Ser Thr
1               5                   10                  15

Pro Pro Leu Leu Pro Ser Ser Pro Ser Pro Ser Pro Ser Pro Ser Gln
            20                  25                  30

Asn Ala Thr Gln Thr Thr Thr Asp Ser Ser Asn Lys Thr Ala Pro Thr
        35                  40                  45

Pro Ala Ser Ser Val Thr Ile Met Ala Thr Asp Thr Ala Gln Gln Ser
    50                  55                  60

Thr Val Pro Thr Ser Lys Ala Asn Glu Ile Leu Ala Ser Val Lys Ala
65                  70                  75                  80

Thr Thr Leu Gly Val Ser Ser Asp Ser Pro Gly Thr Thr Leu Ala
                85                  90                  95

Gln Gln Val Ser Gly Pro Val Asn Thr Thr Val Ala Arg Gly Gly Gly
            100                 105                 110

Ser Gly Asn Pro Thr Thr Thr Ile Glu Ser Pro Lys Ser Thr Lys Ser
            115                 120                 125

Ala Asp Thr Thr Thr Val Ala Thr Ser Thr Ala Thr Ala Lys Pro Asn
        130                 135                 140

Thr Thr Ser Ser Gln Asn Gly Ala Glu Asp Thr Thr Asn Ser Gly Gly
145                 150                 155                 160

Lys Ser Ser His Ser Val Thr Thr Asp Leu Thr Ser Thr Lys Ala Glu
                165                 170                 175

His Leu Thr Thr Pro His Pro Thr Ser Pro Leu Ser Pro Arg Gln Pro
            180                 185                 190

Thr Ser Thr His Pro Val Ala Thr Pro Thr Ser Ser Gly His Asp His
            195                 200                 205

Leu Met Lys Ile Ser Ser Ser Ser Thr Val Ala Ile Pro Gly Tyr
210                 215                 220

Thr Phe Thr Ser Pro Gly Met Thr Thr Thr Leu Glu Thr Val Phe
225                 230                 235                 240

His His Val Ser Gln Ala Gly Leu Glu Leu Leu Thr Ser Gly Asp Leu
            245                 250                 255

Pro Thr Leu Ala Ser Gln Ser Ala Gly Ile Thr Ala Ser Ser Val Ile
            260                 265                 270

Ser Gln Arg Thr Gln Gln Thr Ser Ser Gln Met Pro Ala Ser Ser Thr
            275                 280                 285

Ala Pro Ser Ser Gln Glu Thr Val Gln Pro Thr Ser Pro Ala Thr Ala
        290                 295                 300

Leu Arg Thr Pro Thr Leu Pro Glu Thr Met Ser Ser Ser Pro Thr Ala
305                 310                 315                 320

Ala Ser Thr Thr His Arg Tyr Pro Lys Thr Pro Ser Pro Thr Val Ala
                325                 330                 335

His Glu Ser Asn Trp Ala Lys Cys Glu Asp Leu Glu Thr Gln Thr Gln
            340                 345                 350

Ser Glu Lys Gln Leu Val Leu Asn Leu Thr Gly Asn Thr Leu Cys Ala
            355                 360                 365
```

-continued

Gly Gly Ala Ser Asp Glu Lys Leu Ile Ser Leu Ile Cys Arg Ala Val
            370                 375                 380

Lys Ala Thr Phe Asn Pro Ala Gln Asp Lys Cys Gly Ile Arg Leu Ala
385                 390                 395                 400

Ser Val Pro Gly Ser Gln Thr Val Val Lys Glu Ile Thr Ile His
            405                 410                 415

Thr Lys Leu Pro Ala Lys Asp Val Tyr Glu Arg Leu Lys Asp Lys Trp
            420                 425                 430

Asp Glu Leu Lys Glu Ala Gly Val Ser Asp Met Lys Leu Gly Asp Gln
            435                 440                 445

Gly Pro Pro Glu Glu Ala Glu Asp Arg Phe Ser Met Pro Leu Ile Ile
    450                 455                 460

Thr Ile Val Cys Met Ala Ser Phe Leu Leu Leu Val Ala Ala Leu Tyr
465                 470                 475                 480

Gly Cys Cys His Gln Arg Leu Ser Gln Arg Lys Asp Gln Arg Leu
                485                 490                 495

Thr Glu Glu Leu Gln Thr Val Glu Asn Gly Tyr His Asp Asn Pro Thr
            500                 505                 510

Leu Glu Val Met Glu Thr Ser Ser Glu Met Gln Glu Lys Lys Val Val
            515                 520                 525

Ser Leu Asn Gly Glu Leu Gly Asp Ser Trp Ile Val Pro Leu Asp Asn
530                 535                 540

Leu Thr Lys Asp Asp Leu Asp Glu Glu Asp Thr His Leu
545                 550                 555

<210> SEQ ID NO 2
<211> LENGTH: 7
<212> TYPE: PRT
<213> ORGANISM: Artificial Sequence
<220> FEATURE:
<223> OTHER INFORMATION: PcMab-60 heavy chain CDR1

<400> SEQUENCE: 2

Gly Tyr Ser Phe Thr Asp Tyr
1               5

<210> SEQ ID NO 3
<211> LENGTH: 6
<212> TYPE: PRT
<213> ORGANISM: Artificial Sequence
<220> FEATURE:
<223> OTHER INFORMATION: PcMab-60 heavy chain CDR2

<400> SEQUENCE: 3

Asn Pro Arg Asn Gly Gly
1               5

<210> SEQ ID NO 4
<211> LENGTH: 5
<212> TYPE: PRT
<213> ORGANISM: Artificial Sequence
<220> FEATURE:
<223> OTHER INFORMATION: PcMab-60 heavy chain CDR3

<400> SEQUENCE: 4

Glu Ala Met Glu Tyr
1               5

<210> SEQ ID NO 5
<211> LENGTH: 16
<212> TYPE: PRT

```
<213> ORGANISM: Artificial Sequence
<220> FEATURE:
<223> OTHER INFORMATION: PcMab-60 light chain CDR1

<400> SEQUENCE: 5

Lys Ser Ser Gln Ser Leu Leu Asp Ser Ala Gly Lys Thr Tyr Leu Asn
1               5                   10                  15

<210> SEQ ID NO 6
<211> LENGTH: 10
<212> TYPE: PRT
<213> ORGANISM: Artificial Sequence
<220> FEATURE:
<223> OTHER INFORMATION: PcMab-60 light chain CDR2

<400> SEQUENCE: 6

Arg Leu Met Tyr Leu Val Ser Lys Leu Ala
1               5                   10

<210> SEQ ID NO 7
<211> LENGTH: 9
<212> TYPE: PRT
<213> ORGANISM: Artificial Sequence
<220> FEATURE:
<223> OTHER INFORMATION: PcMab-60 light chain CDR3

<400> SEQUENCE: 7

Trp Gln Gly Thr His Phe Pro Arg Thr
1               5

<210> SEQ ID NO 8
<211> LENGTH: 240
<212> TYPE: PRT
<213> ORGANISM: Artificial Sequence
<220> FEATURE:
<223> OTHER INFORMATION: PcMab-60 light chain

<400> SEQUENCE: 8

Lys Met Met Ser Pro Ala Gln Phe Leu Phe Leu Leu Val Leu Trp Ile
1               5                   10                  15

Arg Glu Thr Asn Gly Asp Val Val Met Thr Gln Thr Pro Leu Thr Leu
                20                  25                  30

Ser Ile Thr Ile Gly Gln Pro Ala Ser Ile Ser Cys Lys Ser Ser Gln
            35                  40                  45

Ser Leu Leu Asp Ser Ala Gly Lys Thr Tyr Leu Asn Trp Leu Leu Gln
        50                  55                  60

Arg Pro Gly Gln Ser Pro Lys Arg Leu Met Tyr Leu Val Ser Lys Leu
65                  70                  75                  80

Ala Ser Gly Val Pro Asp Arg Phe Thr Gly Ser Gly Ser Gly Thr Asp
                85                  90                  95

Phe Thr Leu Lys Ile Thr Arg Val Glu Pro Glu Asp Leu Gly Val Tyr
                100                 105                 110

Tyr Cys Trp Gln Gly Thr His Phe Pro Arg Thr Phe Gly Gly Gly Thr
            115                 120                 125

Lys Leu Glu Ile Lys Arg Ala Asp Ala Ala Pro Thr Val Ser Ile Phe
        130                 135                 140

Pro Pro Ser Ser Glu Gln Leu Thr Ser Gly Gly Ala Ser Val Val Cys
145                 150                 155                 160

Phe Leu Asn Asn Phe Tyr Pro Lys Asp Ile Asn Val Lys Trp Lys Ile
                165                 170                 175

Asp Gly Ser Glu Arg Gln Asn Gly Val Leu Asn Ser Trp Thr Asp Gln
```

```
                180               185                 190
Asp Ser Lys Asp Ser Thr Tyr Ser Met Ser Thr Leu Thr Leu Thr
                    195                 200                 205

Lys Asp Glu Tyr Glu Arg His Asn Ser Tyr Thr Cys Glu Ala Thr His
    210                 215                 220

Lys Thr Ser Thr Ser Pro Ile Val Lys Ser Phe Asn Arg Asn Glu Cys
225                 230                 235                 240

<210> SEQ ID NO 9
<211> LENGTH: 723
<212> TYPE: DNA
<213> ORGANISM: Artificial Sequence
<220> FEATURE:
<223> OTHER INFORMATION: PcMab-60 light chain

<400> SEQUENCE: 9
aaaatgatga gtcctgccca gttcctgttt ctgttagtgc tctggattcg ggaaaccaac      60
ggtgatgttg tgatgaccca gactccactc actttgtcga ttaccattgg acaaccagcc     120
tccatctctt gcaagtcaag tcagagcctc ttagatagtg ctggaaagac atatttgaat     180
tggttgttac agaggccagg ccagtctcca aagcgcctaa tgtatctggt gtctaaactg     240
gcctctggag tccctgacag gttcactggc agtggatcag ggacagattt cacactgaaa     300
atcaccagag tggaacctga ggatttggga gtttattatt gctggcaagg tacacatttt     360
cctcggacgt tcggtggagg caccaagctg gaaatcaaac gggctgatgc tgcaccaact     420
gtatccatct cccaccatc cagtgagcag ttaacatctg gaggtgcctc agtcgtgtgc     480
ttcttgaaca acttctaccc caaagacatc aatgtcaagt ggaagattga tggcagtgaa     540
cgacaaaatg gcgtcctgaa cagttggact gatcaggaca gcaaagacag cacctacagc     600
atgagcagca ccctcacgtt gaccaaggac gagtatgaac gacataacag ctatacctgt     660
gaggccactc acaagacatc aacttcaccc attgtcaaga gcttcaacag gaatgagtgt     720
tag                                                                   723

<210> SEQ ID NO 10
<211> LENGTH: 475
<212> TYPE: PRT
<213> ORGANISM: Artificial Sequence
<220> FEATURE:
<223> OTHER INFORMATION: chPcMab-60 heavy chain

<400> SEQUENCE: 10

Pro Met Ser Ser Pro Gln Ser Leu Ile Thr Leu Thr Leu Asn Met Gly
1               5                   10                  15

Trp Ser Trp Thr Phe Ile Leu Ile Leu Ser Val Thr Thr Gly Val His
                20                  25                  30

Ser Glu Val Gln Leu Gln Gln Ser Gly Pro Glu Leu Val Lys Pro Gly
            35                  40                  45

Ala Ser Val Lys Ile Ser Cys Lys Ala Ser Gly Tyr Ser Phe Thr Asp
        50                  55                  60

Tyr Tyr Met His Trp Val Lys Gln Ser Pro Glu Asn Ser Leu Glu Trp
65                  70                  75                  80

Ile Gly Glu Ile Asn Pro Arg Asn Gly Gly Thr Ser Phe Asn Gln Lys
                85                  90                  95

Phe Trp Gly Lys Ala Thr Leu Thr Val Asp Gln Ser Ser Ser Thr Ala
            100                 105                 110

Tyr Met Gln Leu Lys Ser Leu Thr Ser Glu Glu Ser Ala Val Tyr Tyr
```

```
            115                 120                 125
Cys Ser Asp Glu Ala Met Glu Tyr Trp Gly Gln Gly Thr Ser Val Thr
        130                 135                 140
Val Gly Ser Thr Lys Gly Pro Ser Val Phe Pro Leu Ala Pro Cys Ser
145                 150                 155                 160
Arg Ser Thr Ser Glu Ser Thr Ala Ala Leu Gly Cys Leu Val Lys Asp
            165                 170                 175
Tyr Phe Pro Glu Pro Val Thr Val Ser Trp Asn Ser Gly Ala Leu Thr
        180                 185                 190
Ser Gly Val His Thr Phe Pro Ala Val Leu Gln Ser Ser Gly Leu Tyr
    195                 200                 205
Ser Leu Ser Ser Val Val Thr Val Pro Ser Ser Asn Phe Gly Thr Gln
210                 215                 220
Thr Tyr Thr Cys Asn Val Asp His Lys Pro Ser Asn Thr Lys Val Asp
225                 230                 235                 240
Lys Thr Val Glu Pro Lys Ser Cys Asp Lys Thr His Thr Cys Pro Pro
            245                 250                 255
Cys Pro Ala Pro Glu Leu Leu Gly Gly Pro Ser Val Phe Leu Phe Pro
        260                 265                 270
Pro Lys Pro Lys Asp Thr Leu Met Ile Ser Arg Thr Pro Glu Val Thr
    275                 280                 285
Cys Val Val Val Asp Val Ser His Glu Asp Pro Glu Val Gln Phe Asn
290                 295                 300
Trp Tyr Val Asp Gly Val Glu Val His Asn Ala Lys Thr Lys Pro Arg
305                 310                 315                 320
Glu Glu Gln Tyr Asn Ser Thr Tyr Arg Val Val Ser Val Leu Thr Val
            325                 330                 335
Leu His Gln Asp Trp Leu Asn Gly Lys Glu Tyr Lys Cys Lys Val Ser
        340                 345                 350
Asn Lys Ala Leu Pro Ala Pro Ile Glu Lys Thr Ile Ser Lys Ala Lys
    355                 360                 365
Gly Gln Pro Arg Glu Pro Gln Val Tyr Thr Leu Pro Pro Ser Arg Asp
370                 375                 380
Glu Leu Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
            405                 410                 415
Asn Asn Tyr Lys Thr Thr Pro Pro Val Leu Asp Ser Asp Gly Ser Phe
        420                 425                 430
Phe Leu Tyr Ser Lys Leu Thr Val Asp Lys Ser Arg Trp Gln Gln Gly
    435                 440                 445
Asn Val Phe Ser Cys Ser Val Met His Glu Ala Leu His Asn His Tyr
    450                 455                 460
Thr Gln Lys Ser Leu Ser Leu Ser Pro Gly Lys
465                 470                 475

<210> SEQ ID NO 11
<211> LENGTH: 1428
<212> TYPE: DNA
<213> ORGANISM: Artificial Sequence
<220> FEATURE:
<223> OTHER INFORMATION: chPcMab-60 heavy chain

<400> SEQUENCE: 11
ccaatgtcct ctccacagtc cctgatcaca ctgactctaa acatgggatg gagctggacc      60
```

-continued

```
tttattttaa tcctgtcagt aactacaggt gtccactctg aggtccaact gcagcagtct    120
ggacctgaac tggtgaagcc tggggcttca gtgaagatat cctgcaaggc ttctggttac    180
tcattcactg actactacat gcactgggtg aagcaaagtc ctgaaaatag tcttgagtgg    240
attggagaga ttaatcctag gaatgggggt actagcttca accagaaatt ctggggcaag    300
gccacattaa ctgtagatca atcctccagc acagcctaca tgcagctcaa gagcctgaca    360
tctgaggagt ctgcagtcta ttactgttcg gatgaggcta tggaatactg ggtcaagga    420 acctcagtca ccgtcggatc caccaagggc ccatcggtct tccccctggc gccctgctcc    480
aggagcacct ccgagagcac agcggccctg ggctgcctgg tcaaggacta cttccccgaa    540
ccggtgacgg tgtcgtggaa ctcaggcgct ctgaccagcg gcgtgcacac cttcccagct    600
gtcctacagt cctcaggact ctactccctc agcagcgtgg tgaccgtgcc ctccagcaac    660
ttcggcaccc agacctacac ctgcaacgta gatcacaagc ccagcaacac caaggtggac    720
aagacagttg agcccaaatc ttgtgacaaa actcacacat gcccaccgtg cccagcacct    780
gaactcctgg ggggaccgtc agtcttcctc ttccccccaa acccaagga caccctcatg    840 atctcccgga cccctgaggt cacgtgcgtg gtggtggacg tgagccacga agaccccgag    900
gtccagttca actggtacgt ggacggcgtg gaggtgcata atgccaagac aaagccgcgg    960
gaggagcagt acaacagcac gtaccgtgtg gtcagcgtcc tcaccgtcct gcaccaggac   1020
tggctgaatg gcaaggagta caaatgcaag gtctccaaca aagccctccc agccccatc    1080 gagaaaacca tctccaaagc caagggcag ccccgagaac cacaggtgta caccctgccc   1140
ccatcccggg atgagctgac caagaaccag gtcagcctga cctgcctggt caaaggcttc   1200
tatcccagcg acatcgccgt ggagtgggag agcaatgggc agccggagaa caactacaag   1260
accacgcctc ccgtgctgga ctccgacggc tccttcttcc tttacagcaa gctcaccgtg   1320
gacaagagca ggtggcagca ggggaacgtc ttctcatgct ccgtgatgca tgaggctctg   1380
cacaaccact acacgcagaa gagcctctcc ctgtctccgg gtaaatga              1428
```

<210> SEQ ID NO 12
<211> LENGTH: 34
<212> TYPE: DNA
<213> ORGANISM: Artificial Sequence
<220> FEATURE:
<223> OTHER INFORMATION: Primer

<400> SEQUENCE: 12

```
cggtatcgat aagcttccaa tgtcctctcc acag                                34
```

<210> SEQ ID NO 13
<211> LENGTH: 33
<212> TYPE: DNA
<213> ORGANISM: Artificial Sequence
<220> FEATURE:
<223> OTHER INFORMATION: Primer

<400> SEQUENCE: 13

```
ggcccttggt ggatccgacg gtgactgagg ttc                                 33
```

<210> SEQ ID NO 14
<211> LENGTH: 35
<212> TYPE: DNA
<213> ORGANISM: Artificial Sequence
<220> FEATURE:
<223> OTHER INFORMATION: Primer

```
<400> SEQUENCE: 14
cggtatcgat aagcttaaaa tgatgagtcc tgccc                            35

<210> SEQ ID NO 15
<211> LENGTH: 34
<212> TYPE: DNA
<213> ORGANISM: Artificial Sequence
<220> FEATURE:
<223> OTHER INFORMATION: Primer

<400> SEQUENCE: 15
tctagagtcg cggccgccta acactcattc ctgt                             34
```